(12) United States Patent
Xu et al.

(10) Patent No.: US 6,265,165 B1
(45) Date of Patent: Jul. 24, 2001

(54) METHODS FOR EST-SPECIFIC FULL LENGTH CDNA CLONING

(75) Inventors: Zhidong Xu, San Francisco; Dieter C. Gruenert, Mill Valley, both of CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/240,918

(22) Filed: Jan. 29, 1999

Related U.S. Application Data

(60) Provisional application No. 60/108,183, filed on Nov. 12, 1998.
(51) Int. Cl.$^7$ .................................................. C12Q 1/68
(52) U.S. Cl. .............................................. 435/6; 435/91.2
(58) Field of Search .............................. 435/6, 91.1, 91.2, 435/69.1; 530/350, 351; 536/23.6

(56) References Cited

U.S. PATENT DOCUMENTS

| | | | |
|---|---|---|---|
| 5,759,782 | * 6/1998 | Pastan et al. | 435/6 |
| 5,807,995 | * 9/1998 | Cohen et al. | 530/350 |
| 5,840,531 | * 11/1998 | Vinik et al. | 435/69.1 |
| 5,854,028 | * 12/1998 | Yang et al. | 435/69.52 |
| 5,891,692 | * 4/1999 | Bloom et al. | 435/172.3 |
| 5,936,066 | * 8/1999 | Gubler et al. | 530/351 |
| 6,001,986 | * 12/1999 | Kim et al. | 536/23.6 |
| 6,013,438 | * 1/2000 | Didenko et al. | 435/6 |
| 6,060,240 | * 5/2000 | Kamb et al. | 435/6 |

* cited by examiner

*Primary Examiner*—John S. Brusca
*Assistant Examiner*—Jeffrey S. Lundgren
(74) *Attorney, Agent, or Firm*—Hana Verny

(57) ABSTRACT

A method for cloning of single EST-specific full length cDNA, and/or multiplex-EST-specific full-length cDNA cloning. The method involves cDNA synthesis from highly enriched, homogeneously purified mRNAs and includes hybrid selection for purification of specific mRNAs from total RNA by employing antisense oligonucleotide primers based on expressed sequence tag (EST) sequences.

20 Claims, 9 Drawing Sheets

CFTR

ACTIN

FIG. 10A
FIG. 10B
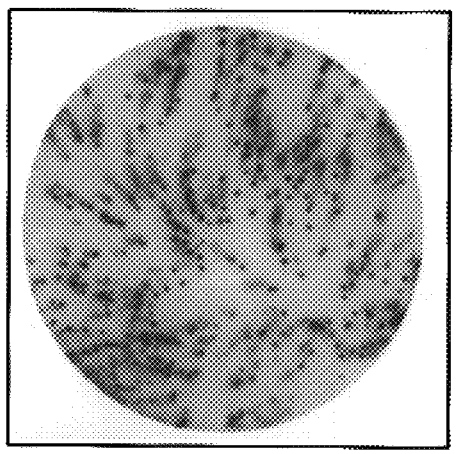
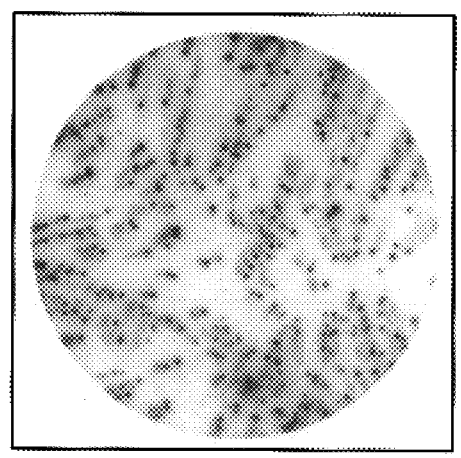

METHODS FOR EST-SPECIFIC FULL LENGTH CDNA CLONING

This application is based on Provisional application Ser. No. 60/108,183 filed Nov. 12, 1998.

This invention was made with Government support under Award Numbers DK 46002 and DK 47766, awarded by the National Institute of Health. The government has certain rights in this invention.

BACKGROUND OF THE INVENTION

1. Field of the Invention

This invention concerns novel methods for cloning of EST-specific full length cDNA. In particular, the invention concerns a method or methods for full-length cDNA cloning and/or full-length cDNA library construction. The method involves cDNA synthesis from highly enriched, homogeneously purified mRNAs and includes hybrid selection for purification of specific mRNAs from total RNA by employing antisense oligonucleotide primers of expressed sequence tag (EST) sequences in a single or multiplex approach.

2. Background and Related Disclosures

Recently, identification and treatment of many human diseases became dependent on identification of gene responsible for the particular disease.

The human genome comprises approximately 100,000 genes. Less than 5% of these genes have been sequenced and assigned biological functions. Large-scale single-pass sequencing of randomly picked cDNA clones has generated over 500,000 human expressed sequence tags (ESTs), as described in *Genome Res.*, 6:807 (1996). These ESTs provide a large reservoir of information on human genes and are potentially powerful tools for discovery of disease genes and regional gene mapping to individual chromosomes. However, limitations of ESTs include redundancy and the partial sequence characteristic that limits the ability to define a given gene's function.

In contrast to the ESTs, full-length cDNA clones and their full-length coding sequences overcome these limitations and provide more accurate information for data base comparisons to determine gene structure, and for analyses predicting gene function. Generation of a comprehensive gene map of expressed sequences also requires cDNA libraries representing a high percentage of full-length mRNA molecules. For large-scale cDNA sequencing, development of full-length cDNA libraries is essential. Some attempts to achieve this are described in *Nature Genet.*, 2:173 (1992) and in *Genome Res.*, 7:353 (1997).

A good example of utility of full-length cDNAs is identification of genes responsible for breast cancer. Breast cancer is one of the most common causes of morbidity and mortality in women. Only a small proportion of breast cancer cases are due to a familial predisposition resulting from mutations in specific genes. The majority of cases are sporadic and appear to involve multiple genetic changes. Defining those genetic changes in terms of initiation and progression is, therefore, essential for understanding the molecular mechanisms that underlie development of breast cancer and its eventual treatment.

Through the Cancer Genomic Anatomy Project (CGAP) a number of expressed sequence tags (ESTs) from genes expressed in normal, precancerous, and cancerous tissues have been generated. The ability to generate high quality, full-length cDNA coding sequences for these ESTs is integral to defining the biological function of these expressed genes.

In an attempt to provide more accurate genetic information, numerous methods have been developed for constructing cDNA libraries from different tissue samples.

Unfortunately, current technologies cannot create representational libraries of full-length cDNAs and are therefore limited in their utility. cDNA library screening using currently available methods can be very laborious and time-consuming, and as a result, these technologies are not readily amenable to large scale full-length cDNA cloning and sequencing.

Therefore, a method that streamlines this process would greatly facilitate the generation of full-length cDNAs and full-length coding sequences, leading to a better understanding of the genetic and metabolic mechanisms that underlie breast cancer and other genetic or genetically controlled diseases.

Successful cloning of a specific, full-length cDNA largely depends on the frequency of full-length cDNA molecules within a cDNA library. Of the numerous methods for construction of cDNA libraries, the approach based on methods described in *Gene*, 25:263 (1983) is the most widely used.

The mRNA complexity of a typical cell is represented in 15,000–20,000 distinct mRNAs. The most prevalent mRNAs are present at approximately 5000 copies per cell and low abundance mRNA are generally at 1–15 copies per cell. Because of heterogeneous expression in the cells that comprise a given organ, mRNA can be even more underrepresented in certain tissues, as described, for example, in *Brain Res. Rev.*, 17:263 (1992) for the brain cells.

This heterogeneity makes it difficult to isolate specific, low abundance mRNAs. To some extent, such limitation can be circumvented by isolating mRNAs from clonal cell lines. However, generating cDNA libraries from cell lines is often not possible or will not address the case where the expression level of a given mRNA-derived sequence is undefined.

It is, therefore, important that other approaches are developed which are able to isolate full-length cDNA clones of those cells having undefined expression level of mRNA sequence.

Several different techniques have been developed to facilitate cloning of full-length cDNA and to enrich rare mRNA represented in conventional cDNA libraries. The rapid amplification of cDNA ends (RACE) technique has been used for cloning of missing ends from a known incomplete cDNA sequence, as described in *PNAS (USA)*, 85:8998 (1988). However, this approach requires a substantial effort to generate the full-length cDNA clones by attaching RACE-generated fragments onto a cDNA clone that contains a partial sequence.

Approaches to achieve enrichment of specific sequences include subtractive cDNA libraries (*Trends Genet.*, 9:70 (1993)) and normalized cDNA libraries (*Genome Res.*, 6:791 (1996)). While subtractive and normalized libraries are generally not full-length cDNAs, the frequency of full-length cDNAs has been increased by RecA-mediated triple-strand formation in a subtractive cDNA library (*Nucleic Acid Res.*, 24:3478 (1996)).

Though these different approaches have been employed, current technologies have not yet been able to efficiently produce representative libraries of full-length cDNAs.

Therefore, a primary objective of this invention is to provide a novel approach for generation and cloning of full-length cDNA which either allows easier full length cDNA cloning or which circumvents altogether the need for cDNA libraries representing all cellular mRNA species by relying on enrichment of specific mRNAs from any tissue or cell source.

All patents, patent applications and publications described or referred to in the specification are hereby incorporated by reference.

SUMMARY OF THE INVENTION

One aspect of the current invention concerns a method for cloning of single or multiple EST-specific full-length cDNA.

Another aspect of the current invention concerns a method for rapidly constructing EST-specific full-length cDNA clones.

Yet another aspect of the current invention concerns a method for full-length cDNA cloning by isolating expressed sequence tag (EST) specific mRNA from total RNA using end-labeled antisense primers conjugated to solid support, purifying said mRNA, synthesizing the full-length cDNA from the purified mRNA and cloning said cDNA into a vector.

Still another aspect of the current invention concerns a method for synthesis of EST-specific full-length cDNA, said method comprising steps of obtaining total cellular RNA, submitting total cellular RNA to hybridization with biotinylated EST-specific antisense primers to obtain EST-specific mRNA, isolating and purifying EST-specific mRNA by contacting the hybridized product with streptavidin containing solid phase, and submitting the EST-specific mRNA to cDNA cloning.

Still yet another aspect of the current invention concerns a method for synthesis of EST-specific full-length cDNA wherein the cDNA cloning comprises synthesis of a first strand cDNA by reverse transcription of the EST-specific mRNA and synthesis of a second strand cDNA by $E.$ $coli$ DNA polymerase I.

Still another aspect of the current invention concerns a method for synthesis of EST-specific full-length cDNA wherein the cDNA cloning comprises synthesis of a first strand cDNA by reverse transcription of the EST-specific mRNA and synthesis of a second strand cDNA by T7 DNA polymerase I wherein the EST-specific primers are designed based on ESTs and labeled at their 5' end or 3' end with solid support.

Still another aspect of the current invention concerns a method for construction and cloning of a single EST-specific full-length cDNA, said method comprising the steps of:

(a) preparing EST-specific antisense primers and biotinylating said primers at the 5' end or at the 3' end;
(b) obtaining total cellular RNA;
(c) submitting total cellular RNA to hybridization with one biotinylated EST-specific antisense primer to obtain a single EST-specific mRNA;
(d) purifying EST-specific mRNA by contacting a hybridized product with a solid phase, such as, for example, streptavidin coated magnetic beads;
(e) isolating the EST-specific mRNA by eluting and washing the hybridized product from the solid phase;
(f) synthesizing a first cDNA strand by submitting the isolated EST-specific mRNA to reverse transcription using synthesis primers, such as, for example, Not I oligo(dT)$_{18}$ PstI oligo (dt)$_{18}$, or oligo d(T)$_{12-18}$;
(g) synthesizing a second cDNA strand by $E.$ $coli$ DNA polymerase I in the presence of RNase H or synthesizing a poly(dT) using 3' terminal deoxynucloeotide transferase synthesizing a second cDNA strand by using T7 DNA polymerase;
(h) purifying double-stranded cDNA;
(i) blunting cDNA ends by polymerase, such as T$_4$ DNA polymerase or pfu DNA polymerase;
(j) optionally, ligating a primer adaptor, such as, EcoRI, to the cDNA ends by ligase, such as T$_4$ ligase;
(k) cloning the cDNA into a vector, such as plasmid vector, phage λ vector or mammalian cell expressed plasmid vector;
(l) transforming the vector containing cDNA into bacterial competent cells, for example, by chemical treatment or by electroporation;
(m) screening full-length cDNA clones by PCR amplification or screening full-length cDNA clones by colony hybridization using EST-specific probes, such as, radioactive, chemiluminescent or fluorescent probes; and
(n) sequencing DNA of EST-specific full-length cDNA clones.

Still yet another aspect of the current invention is the multiplex EST-specific full-length cDNA cloning, said method comprising steps of:

(a) preparing EST-specific antisense primers and biotinylating said primers at the 5' end or at the 3' end;
(b) obtaining total cellular RNA;
(c) submitting total cellular RNA to hybridization with multiple biotinylated EST-specific antisense primers to obtain multiplex EST-specific mRNAs;
(d) purifying EST-specific mRNA by contacting a hybridized product with a solid phase, such as, for example, streptavidin coated magnetic beads;
(e) isolating the multiplex EST-specific mRNAs by eluting and washing the hybridized products from the solid phase;
(f) synthesizing a first cDNA strand by submitting the isolated EST-specific mRNA to reverse transcription using synthesis primers, such as, for example, Not I oligo(dT)$_{18}$ Pst I oligo (dT)$_{18}$ or oligo d(T)$_{12-18}$;
(g) synthesizing a second cDNA strand by $E.$ $coli$ DNA polymerase I in the presence of RNase H;
(h) purifying double-stranded cDNA by phenol/chloroform extraction;
(i) blunting cDNA ends by a polymerase, such as T$_4$ DNA polymerase or pfu DNA polymerase;
(j) optionally, ligating a primer adaptor, such as, EcoRI, to the cDNA ends by ligase, such as T$_4$ DNA ligase;
(k) cloning the cDNA into a vector, such as plasmid vector, phage λ vector or mammalian cell expressed plasmid vector;
(l) transforming the vector containing cDNA into bacterial competent cells, for example, by chemical treatment or by electroporation;
(m) screening full-length cDNA clones by PCR amplification or screening full-length cDNA clones by colony hybridization using EST-specific probes, such as, radioactive, chemiluminescent or fluorescent probes; and
(n) sequencing DNA of EST-specific full-length cDNA clones.

BRIEF DESCRIPTION OF THE FIGURES

FIG. 10 illustrates actin cDNA—colony hybridization.

DEFINITIONS

Figure 1:
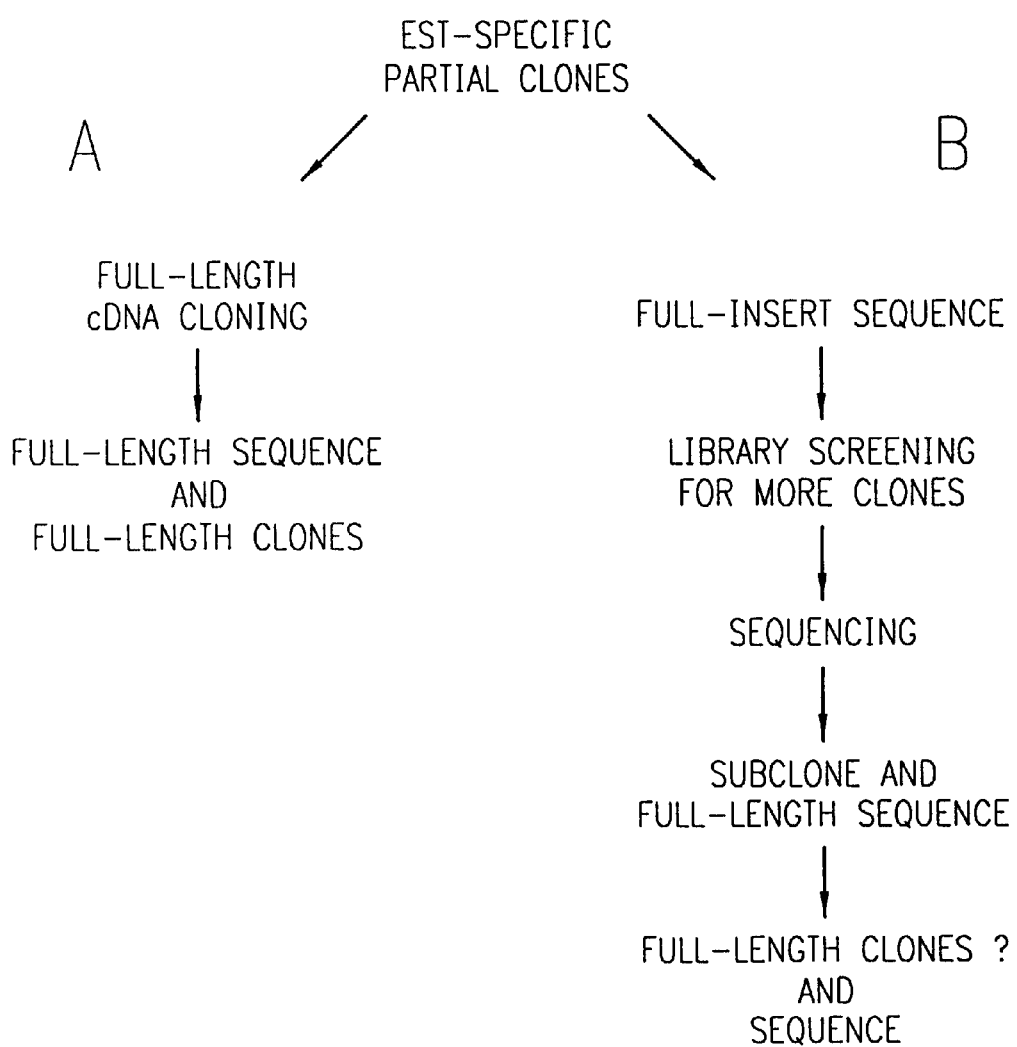
FIG. 1 is a scheme comparing a method of the invention (FIG. 1A) with conventional strategies (FIG. 1B) for generating full-length amino acid coding sequences.

As used herein:

"EST" means expressed sequence tag.

"RACE" means rapid amplification of cDNA ends technique.

"SSC" means sodium chloride/sodium citrate mixture.

DETAILED DESCRIPTION OF THE INVENTION

This invention has been developed in order to provide methods for rapidly constructing EST-specific full-length cDNA clones.

A large number of human ESTs generated so far have facilitated the identification of disease genes and regional gene mapping to individual chromosomes. However, ESTs have their limitations. The primary limitations of ESTs are the redundancy and the nature of partial sequence which is often not adequate to assess the gene's function. The development of full-length cDNA clones is thus needed to produce complete gene sequence specific to a particular EST, thereby providing a prerequisite for testing the gene's biological functions.

Until now, however, current technologies could not efficiently produce representational libraries of full length cDNAs. Library screening available to date is limiting as it is very laborious and time consuming and consequently is not practical for a large scale full length cDNA cloning.

Briefly, the current methods of the invention for a rapid and efficient cloning of full-length cDNAs allow the enrichment and isolation of EST-specific mRNA from total RNA using antisense oligonucleotide primers conjugated to solid support. Full-length cDNAs corresponding to the ESTs are then cloned from in vitro purified mRNA.

The advantage of the current method is that a full-length cDNA can be synthesized more feasiblely from a homogeneously purified mRNA than from a pool of highly heterogeneously mRNAs. Since the cDNA clones in this method are directly derived from highly enriched mRNA, screening for a cDNA clone using this approach is much easier and cost-effective than conventional library screening, making it feasible for large scale full-length cDNA cloning. Since even the rarest expressed mRNA could be enriched from total cellular RNA using the current method, the cDNA representation of that particular mRNA is preserved. This method is also easily adaptable for full-length cDNA cloning provided that a partial cDNA sequence is available.

The method for full length cDNA cloning is suitable for both the single and multiplex EST cloning.

I. Method or Full-Length cDNA Cloning: Single EST Based Approach

The method for full-length cDNA cloning according to the invention utilizes numerous human EST sequences.

A method of the invention enables a rapid cloning of any EST-specific full-length cDNAs directly from total cellular RNA without library construction. The principle of the method is the use of antisense oligonucleotide primers. To capture EST-specific mRNAs, the full-length cDNAs are then synthesized from these purified mRNAs and cloned into vectors. The antisense oligonucleotide primers are designed based on available ESTs or on partial cDNA sequences.

The antisense primers are conjugated to the solid phase support, such as biotin/streptavidin magnetic beads or chromatography columns. The EST-specific mRNA is purified and isolated by molecular hybridization of antisense primer and solid phase capture, or digoxygenin-antidigoxygenin magnetic beads are used. Full-length cDNA corresponding to the EST is then synthesized from the purified mRNA and cloned into a vector using methods known in the art.

Reverse transcription of enriched mRNA resulting in full-length cDNA clones, utilized by the current method, is much more efficient and complete than non-enriched pooled mRNA used in ordinary cDNA library construction.

Representation of mRNA species is assured since a rarest mRNA, even one copy per cell, can be enriched and isolated in vitro for cDNA cloning. This feature is particularly important in cloning of rare expressed mRNA if their frequency is below $10^{-6}$. These low abundance mRNAs are normally very difficult to isolate from a cDNA library.

The method comprises two basic steps, as illustrated in FIG. 1A. In the first step, EST-specific, full-length cDNA clones are isolated using a library-free system of the invention. In step two, high quality coding sequences are generated and confirmed, and the full-length cDNA clones are available for gene functional analysis.

Simplicity of the method is easily ascertainable by comparison to other currently used conventional methods used for obtaining full-length clones and sequences, as illustrated in FIG. 1B. These methods involve several rather complicated steps, such as obtaining full-insert sequence from EST-specific partial clones, library screening for more clones, sequencing, subcloning and generating full-length sequence, obtaining full-length clones and sequences. In the conventional strategy, thus, full-inserts of candidate EST-specific clones must be sequenced, more clones must be screened for from cDNA libraries and sequenced and, additionally, to obtain full-length clones and to cover full-length coding sequences, subcloning is required.

As seen from the comparison presented in FIG. 1A and FIG. 1B, the current method is easy, fast and technically undemanding.

Figure 2:
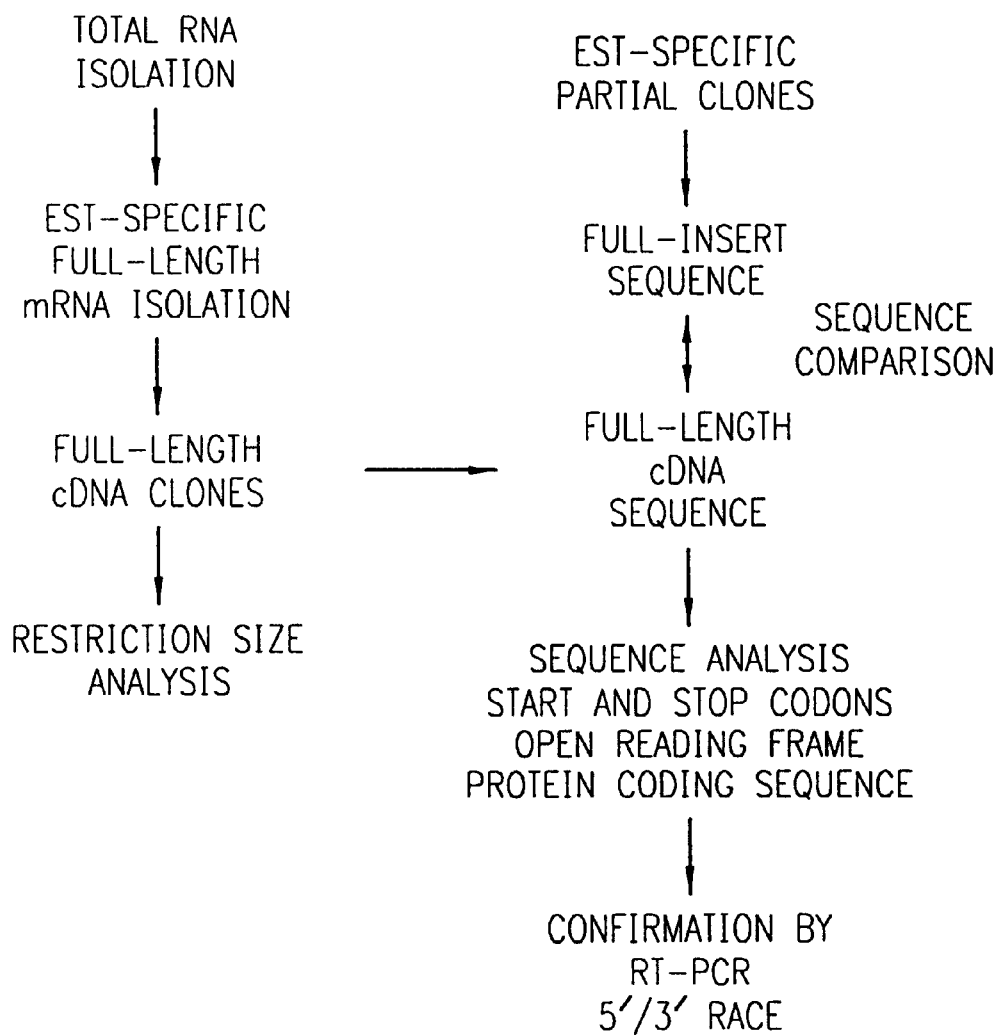
FIG. 2 illustrates overall procedure involved in the method of full-length cDNA cloning and sequencing.

A general procedure for cloning EST-specific, full-length cDNA for relevant genes and for generating high quality coding sequences from those full-length cDNA clones is illustrated in FIG. 2. FIG. 2 schematically illustrates an overall procedure for full length cDNA cloning and sequencing according to the invention. Individual specific procedures are described in Examples 1–12.

Briefly, to clone EST-specific full-length cDNAs, total RNA or total cytoplasmic RNA is isolated from cells and/or tissue. EST-specific full-length mRNA is isolated from total RNA with biotin labeled antisense primers conjugated to streptavidin coated magnetic beads and purified. The cDNA is synthesized from the purified EST-specific mRNA and then cloned into plasmid or λ phage vectors. Recombinant cDNA clones carrying the EST-specific mRNAs are identified by PCR amplification screening of pooled bacterial colonies or by colony hybridization. Plasmid DNA is isolated from clones containing cDNA inserts and analyzed by restriction enzyme digestion for size distribution.

High qualify sequences are generated from putative full-length clones by sequencing dialysis. The coding sequences are analyzed to identify start and stop cordons, the potential open reading frame (ORF), and the gene structure. The integrity of the cDNA sequences and clones in terms of their full-length character is confirmed by additional analyses including RT-PCR and 5' to 3' rapid amplification of cDNA ends using RACE.

In detail, the single approach method for cloning of full-length cDNA comprises the following steps:

(a) preparing EST-specific antisense primers and biotinylating said primers at the 5' end or at the 3' end;

(b) obtaining total cellular RNA;

(c) submitting total cellular RNA to hybridization with biotinylated EST-specific antisense primer to obtain single EST-specific mRNA;

(d) purifying EST-specific mRNA by contacting a hybridized product with a solid phase, such as, for example, streptavidin coated magnetic beads;

(e) isolating the EST-specific mRNA by eluting and washing the hybridized product from the solid phase;

(f) synthesizing a first cDNA strand by submitting the isolated EST-specific mRNA to reverse transcription using synthesis primers, such as, for example, Not I oligo(dT)$_{19}$, Pst I oligo (dt)$_{18}$ or oligo d(T)$_{12-18}$;

(g) synthesizing a second cDNA strand by *E. coil* DNA polymerase I in the presence of RNase H or synthesizing a poly(dT) using 3' terminal deoxynucloeotide transferase synthesizing a second cDNA strand by using T7 DNA polymerase;

(h) purifying double-stranded cDNA by phenol/chloroform extraction;

(i) blunting cDNA ends by DNA polymerase, such as T$_4$ DNA polymerase or pfu DNA polymerase;

(j) optionally, ligating a primer adaptor, such as, EcoRI, to the cDNA ends by DNA ligase, such as T$_4$ DNA ligase;

(k) cloning the cDNA into a vector, such as plasmid vector, mammalian cell expressed plasmid vector or phage λ vector;

(l) transforming the vector containing cDNA into bacterial competent cells, for example, by chemical treatment or by electroporation;

(m) screening full-length cDNA clones by PCR amplification or screening full-length cDNA clones by colony hybridization using EST-specific probes, such as, radioactive, chemiluminescent or fluorescent probes; and (n) sequencing DNA of EST-specific full-length cDNA clones.

A. Enrichment, Purification and Isolation of EST-Specific Full-length mRNA

Figure 3:
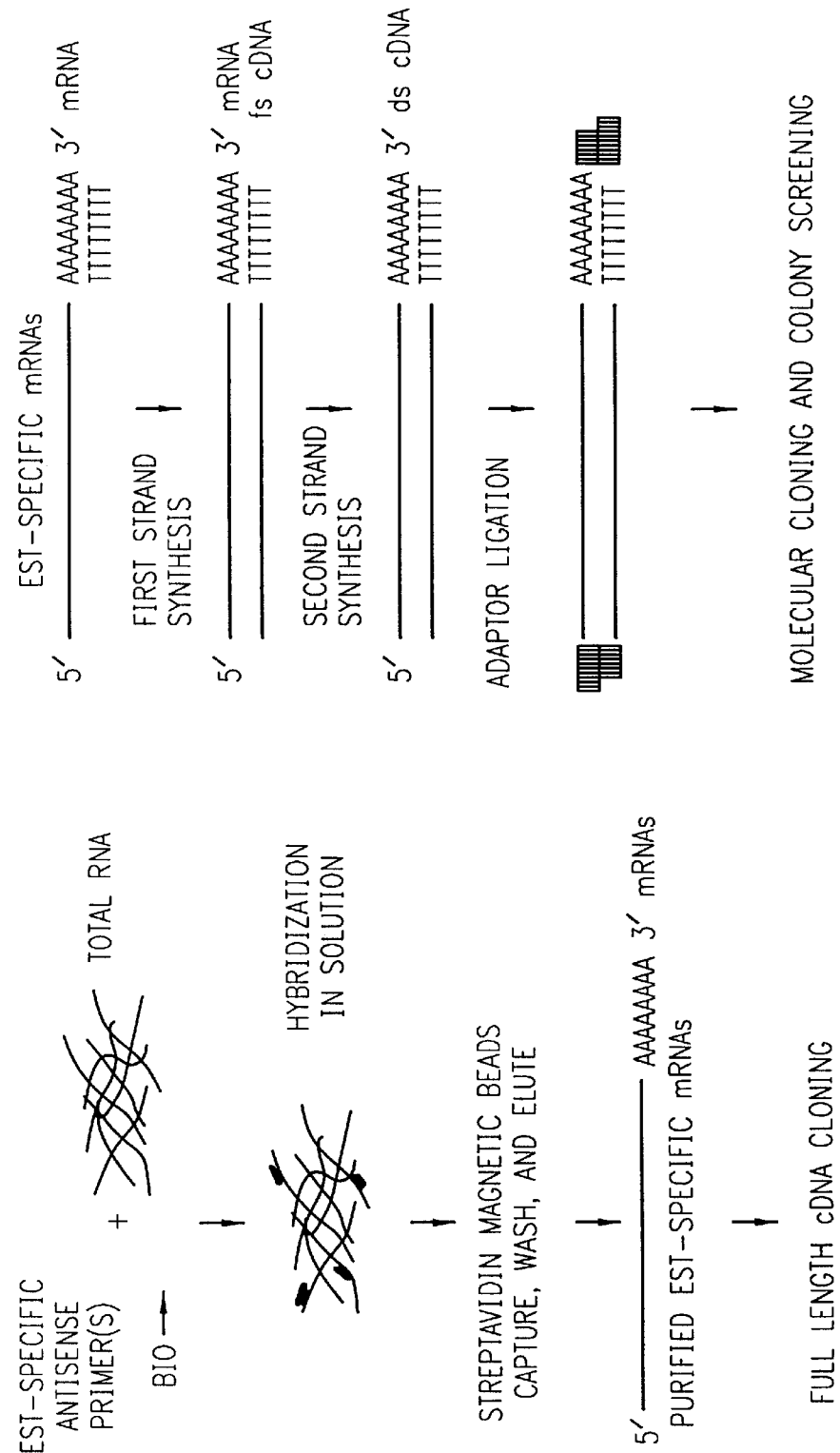
FIG. 3 is a schematic diagram of the library-free system for cloning EST-specific full-length cDNAs.

Methods for enrichment and isolation of EST-specific mRNA are essential for the full-length cDNA cloning of this invention. FIG. 3 is a schematic diagram of the library-free system for cloning full-length cDNA. Steps and procedures involved in enrichment and isolation of full-length mRNA are described in detail below and in the Examples.

As seen in FIG. 3, EST-specific mRNAs are purified from total cellular RNA by a solid-phase support using biotinylated antisense primers conjugated on solid support, such as streptavidin coated magnetic beads. The purified EST-specific mRNAs are then reverse transcribed into first strand cDNA using oligo(dT) primer. After the second strand synthesis, double stranded cDNA is cloned into a vector. The cDNA clone is then detected by PCR and full-length cDNA are identified by sequence analysis of the recombinant clones.

1. Isolation of Total RNA, Cytoplasmic RNA and poly (A)$^+$ RNA

Total RNA is isolated from cells, preferably from cultured human cells or tissue. For purposes of developing and testing this invention, two cell lines were used as models. The two lines human cervical carcinoma fibroblast cell line HeLa and a human airway epithelial cell line, 16HBE14o$^-$ (*Amer. J. Rep. Cell Mol. Biol.*, 10:38–47 (1994)). Total RNA was isolated according to the manufacturer's instructions using RNeasy kit (Qiagen, Chatsworth, Calif.). Poly(A)$^+$ RNA was isolated from total RNA by oligo(dT) cellulose columns using Micro-Poly(A)Pure kit (Ambion, Austin, Tex.). The other cells to be a source of the total RNA are treated in the same way. The exact procedure is described in *Gene Ther.*, 3:859 (1996).

In a generally useful procedure, cytoplasmic RNA isolated from cells in culture using NP-40 (Sigma Chemicals) to lyse the cells. Briefly, about 10$^7$ cells (e.g. HeLa, 16HBE14o$^-$) are trypsinized from T75 culture dishes and washed three times with cold (4° C.) Mg- and Ca-free phosphate buffered saline (PBS). Cell pellets were resuspended in 0.5 ml of ice-cold lysis solution of 0.14 M NaCl, 1.5 mM MgCl$_2$, 10 mM Tris (pH 7.8), 10% NP40, and mixed gently by pipetting. After incubating on ice for 5 minutes, nuclei were removed by centrifugation at 2000×g for 5 minutes at 4° C. The supernatant containing the cytoplasmic RNA was transferred to a 1.5-ml microfuge tube. To eliminate residual DNA, the cytoplasmic RNA supernatant was treated by adding 1 μl (1 unit) of RNase-free DNase 1 (Promega) and incubating at 37° C. for 15 minutes. After treatment with RNase-free DNase 1, the RNA supernatant was mixed with 25 μl of 20% SDS (to 1%), 10 μl of 0.5 M EDTA, and 4 μl of 10 mg/ml proteinase K, and incubated in a water bath for 15 minutes at 50° C. The RNA solution was extracted once with 500 μl of phenol/chloroform (1:) and the supernatant was transferred to a fresh 1.5-ml microfuge tube. The RNA was precipitated by addition of 4 μl of 5 M NaCl, 3 μl of 1 M MgCl$_2$ and 2.5 volumes of ethanol. After incubating at −20° C. for 30 minutes, the RNA was pelleted by centrifugation at 10,000×g for 15 minutes at 4° C., washed with 1 ml of cold 70% ethanol, air dried and resuspended in diethylpyrocarbonate (DEPC) treated water. RNA was quantified by UV spectrophotometry.

2. EST-Specific Oligonucleotide Primers

Examples of oligonucleotide primers used for full-length cDNA cloning are listed in Table 1. These primers are based on human chromosome 7 EST data base which have been assigned on the chromosome 7q31 region (*Genome Res.*, 7:281–292 (1997)).

Table 1 lists oligonucleotide primers, sense and antisense (reversed). Antisense primers are biotinylated as described in Example 3. Primers are identified by their EST name.

TABLE 1

Oligonucleotide Primers, Sense and Antisense

| EST Name | Forward (+) | | Reverse (−) 5'biotinylated | | PCR Size(bp) |
|---|---|---|---|---|---|
| 7B04H06 | TCTAGGCAGAGTCTCAGGAGCA | SEQ ID NO:1 | AGGGAGGTTTGTCCTGAAATGG | SEQ ID NO:2 | 344 |
| 7B04F03 | ACTTGGCTCCTCTCACTTGGAA | SEQ ID NO:3 | GTGTAGTAGTAAAGAGGAGAGG | SEQ ID NO:4 | 279 |
| 7B03D05 | TTCAACCTCAGCCTCCCCTTCA | SEQ ID NO:5 | CCATGGGTTCATGTGTGATTGA | SEQ ID NO:6 | 196 |
| 7B07A01 | CTTAGCAAGGGCAGGCTGATGT | SEQ ID NO:7 | CTCCAACCATGGCACTCAGATA | SEQ ID NO:8 | 267 |
| 7B09C01 | AGGACAGGTAGGAGGATGGGGT | SEQ ID NO:9 | CTCTCCTCTCACTCATTCTCTT | SEQ ID NO:10 | 151 |
| 7B45A09 | TCTGGGTCAGTGATAGAGAATG | SEQ ID NO:11 | AGGATGGCATCCTATGAAATGC | SEQ ID NO:12 | 194 |
| 7H01C12 | GGATGATGACTTGGTGTGAATC | SEQ ID NO:13 | CTGTGAAGACCGTGAGATGATT | SEQ ID NO:14 | 264 |
| 7P01A06 | TTGAGACACTTAACCTCCCGG | SEQ ID NO:15 | CTAGGGAAGTTTCCATTGTTCC | SEQ ID NO:16 | 290 |
| 7P01G11 | GTCAAGGATGACTCTCCAATTT | SEQ ID NO:17 | TTCCCTCAAGCTTCCAGTTTAC | SEQ ID NO:18 | 206 |
| 7P02D11 | GAAGGAGAGCAAGTTCAAGAGC | SEQ ID NO:19 | CCATGACAGACCTGAAGACATG | SEQ ID NO:20 | 250 |

PCR size (bp) denotes a PCR fragment amplified by the forward and reverse primer Primer sequences from 29 putative breast cancer-specific ESTs are listed in Table 2.

These breast cancer specific ESTs were selected from the Cancer Genomic Anatomy Project under the category of Genes of Interest. There are a total of 7,500 ESTs being generated from breast tumor libraries. Of these, about 50 sequences have been defined as genes of interest. These sequences are highly represented (>1%) in and are unique to the breast tumor libraries. Elucidation of these genes of interest at the molecular level may provide important insights to the roles that these genes play in the initiation and progression of breast cancer. The entry name (EST name) of each EST is given together with UniGen, GenBank and IMAGE entries.

TABLE 2

Designed Primers Based on Breast Cancer Specific ESTs

| IMAGE # | GenBank | dbEST | UniGene | Primer Sequence (5'->3') | |
|---|---|---|---|---|---|
| 1056518 | AA557247 | 1207628 | Hs.71943 | (+) 5'-GTGGCTTGTAAATCATTCTCCTGT-3' | SEQ ID NO: 21 |
| | | | 104 bp** | (−) 5'Bio-TCTGAGGGTTTATTGGTCAGGG-3' | SEQ ID NO: 22 |
| 1131081 | AA610599 | 1308300 | Hs.3226 | (+) 5'-TTCCATTGCTGCAGATGTAAAGG-3' | SEQ ID NO: 23 |
| | | | 442 bp | (−) 5'Bio-TGTGTCTTCCATTCTGCTTTGC-3' | SEQ ID NO: 24 |
| 1131265 | AA633532 | 1335648 | Hs.123823 | (+) 5'-TGTCTTCTAAGGATGGTCTTCCA-3' | SEQ ID NO: 25 |
| | | | 286 bp | (−) 5'Bio-GATTAAGTTCATGCATTTCTACAC-3' | SEQ ID NO: 26 |
| 1132291 | AA631748 | 1330056 | Hs.116465 | (+) 5'-GCTTTATAGTGTAACAGAATGGGC-3' | SEQ ID NO: 27 |
| | | | 224 bp | (−) 5'Bio-CGTTTCTAAAGAACAGAGAGGCG | SEQ ID NO: 28 |
| 1131590 | AA633382 | 1335464 | Hs.116345 | (+) 5'-TGAAGGGGTACTGTACTTTATTCC-3' | SEQ ID NO: 29 |
| | | | 205 bp | (−) 5'Bio-ACTAGACTGAGAGCCAGTGTGA-3' | SEQ ID NO: 30 |
| 1157626 | AA627362 | 1325736 | Hs.116190 | (+) 5'-AGGGGAGCCGAATTCTACATTTC-3' | SEQ ID NO: 31 |
| | | | 114 bp | (−) 5'Bio-TTTATTACAGCAACTGAGGCG3' | SEQ ID NO: 32 |
| 1057188 | AA593676 | 1271686 | Hs.115962 | (+) 5'-GACTGGATGTGCCTTTATCCTCT-3' | SEQ ID NO: 33 |
| | | | 311 bp | (−) 5'Bio-ATACGCCTTCTCATCCACCAGA-3' | SEQ ID NO: 34 |
| 1097887 | AA587491 | 1263686 | Hs.115950 | (+) 5'-GAGCTGCAAGTGATGACAGCAT-3' | SEQ ID NO: 35 |
| | | | 253 bp | (−) 5'Bio-GCGGTGATGACTCTTGAACTTC-3' | SEQ ID NO: 35 |
| 1030084 | AA587420 | 1263615 | Hs.115949 | (+) 5'-GTGAATGTGAAGTTCCCCATCTT-3' | SEQ ID NO: 36 |
| | | | 113 bp | (−) 5'Bio-ACAGAGGTGTCAAGGGTAGGA-3' | SEQ ID NO: 37 |
| 967053 | AA507019 | 1151720 | Hs.115699 | (+) 5'-GGCCGATTTTGTCCAGAATTATCT-3' | SEQ ID NO: 38 |
| | | | 350 bp | (−) 5'-Bio-TCTTGCGAGGAGGTCGTGAGAA-3' | SEQ ID NO: 39 |
| 1098334 | AA614419 | 1312120 | Hs.112840 | (+) 5'-AAGTAACAGCAGCCGTCTTGGA-3' | SEQ ID NO: 40 |
| | | | 288 bp | (−) 5'Bio-GAGAACACAAGGACTCTACCCA-3' | SEQ ID NO: 41 |
| 1131239 | AA610317 | 1308018 | Hs.112825 | (+) 5'-TGTCCACACTGACTGGAATACT-3' | SEQ ID NO: 42 |
| | | | 330 bp | (−) 5'BioCGGAATGATCTCAGTAACTATTTTCC | SEQ ID NO: 43 |
| 1131131 | AA610143 | 1307844 | Hs.112822 | (+) 5'-GCACAAGGATGTCACGGGATATT-3' | SEQ ID NO: 44 |
| | | | 233 bp | (−) 5'Bio-CCACACCTACACACCTCTACAC-3' | SEQ ID NO: 45 |
| 1098126 | AA603773 | 1298429 | Hs.112559 | (+) 5'-TCCAAGACCTGGCCTCCCTTAA-3' | SEQ ID NO: 46 |
| | | | 244 bp | (−) 5'Bio-CTGGCAACTGCAGGGCACTGT-3' | SEQ ID NO: 47 |
| 1098112 | AA601515 | 1294256 | Hs.112541 | (+) 5'-CAAATACAGTTAATAAGAGAGTATTAG | SEQ ID NO: 48 |
| | | | 212 bp | (−) 5'Bio-TGCTTGATGGTGCCTCCGATCT-3' | SEQ ID NO: 49 |
| 1198105 | AA601521 | 1294262 | Hs.112420 | (+) 5'-GGGCAATCATGTCATTTAATAATCA | SEQ ID NO: 50 |
| | | | 249 bp | (−) 5'Bio-CTCAAAAGTCCATGACAAATAGAAG | SEQ ID NO: 51 |
| 1056699 | AA574091 | 1224491 | Hs.105964 | (+) 5'-CGCAGAATCAAAGTCTGTACTTCAA-3' | SEQ ID NO: 52 |
| | | | 273 bp | (−) 5'Bio-CCCAAACCCTTATGCATTTTATGC-3' | SEQ ID NO: 53 |
| 1071563 | AA569963 | 1220449 | Hs.105943 | (+) 5'-CATGAAGCTACAGATCTTAGTGCT-3' | SEQ ID NO: 54 |
| | | | 262 bp | (−) 5'Bio-CCAGGGCCTTGGACTGTTTC-3' | SEQ ID NO: 55 |
| 1071558 | AA569957 | 1220443 | Hs.105942 | (+) 5'TCATTATCTCTACCGTGGTTCTGT-3' | SEQ ID NO: 56 |
| | | | 233 bp | (−) 5'Bio-TCTACCTGCATTACAAACCCCTAT-3' | SEQ ID NO: 57 |
| 1056316 | AA558935 | 1209606 | Hs.105885 | (+) 5'-AGTGTCAGGGTGACCAGGAATT-3' | SEQ ID NO: 58 |
| | | | 188 bp | (−) 5'Bio-GCCTGGAGTTAAGTATTCTGAAAT3' | SEQ ID NO: 59 |
| 1057055 | AA557340 | 1207721 | Hs.105880 | (+) 5'-AGCGGGCCGTATCTCCTTGTC-3' | SEQ ID NO: 60 |
| | | | 135 bp | (−) 5'BioGACAAAATAGGGATAGGGAGATTC3' | SEQ ID NO: 61 |

TABLE 2-continued

Designed Primers Based on Breast Cancer Specific ESTs

| IMAGE # | GenBank | dbEST | UniGene | Primer Sequence (5'->3') | |
|---------|---------|-------|---------|--------------------------|---|
| 1056430 | AA557173 | 1207554 | Hs.105879 202 bp | (+) 5'GGGAGAGAAACCCTATGAGTGT-3'<br>(−) 5'Bio-AGAATCTTGGCAGATCTGAAGG-3' | SEQ ID NO: 62<br>SEQ ID NO: 63 |
| 967492 | AA514945 | 1159661 | Hs.105466 280 bp | (+) 5'-TGATCATCTTTGGGGTGGCAGA-3'<br>(−) 5'-Bio-CTTGTTCTGAAACTGGCAGCTC | SEQ ID NO: 64<br>SEQ ID NO: 65 |
| 966738 | AA505898 | 1150528 | Hs.105453 265 bp | (+) 5'-TCACAGCATGGTGGCCTCTAG-3'<br>(−) 5'-Bio-GACACAAATTCAAATGGCTGTGGT3' | SEQ ID NO: 66<br>SEQ ID NO: 67 |
| 966335 | AA505486 | 1150116 | Hs.105452 220 bp | (+) 5'-CTTAGTGTTAGGTTGTCTGATGAG-3'<br>(−) 5'Bio-GGGAATGCTACAATGTCAGACA-3' | SEQ ID NO: 68<br>SEQ ID NO: 69 |
| 965839 | AA512935 | 1157586 | Hs.105445 359 bp | (+) 5'-GAACGACCTAGAAGAGTGCTTG-3'<br>(−) 5'Bio-AGGAGCAGCCATTGATTTTGTG-3' | SEQ ID NO: 70<br>SEQ ID NO: 71 |
| 1030007 | AA559040 | 1209711 | Hs.103763 239 bp | (+) 5'-AGATGATTTCCCTTCTGTAACTCC-3'<br>(−) 5'Bio-CTTAAGTGGGGTTTCAGAACAGAT3' | SEQ ID NO: 72<br>SEQ ID NO: 73 |
| 1056561 | AA557284 | 1207665 | Hs.101283 184 bp | (+) 5'-TCTCAGCTCTGCAGCTGTCTG-3'<br>(−) 5'Bio-CCAACATACCCCTTTCTGGTGT-3' | SEQ ID NO: 74<br>SEQ ID NO: 75 |
| 1030064 | AA587404 | 1263599 | Hs.123816 155 bp | (+) 5'-TAAACGGAATCACGTATGGTTCTT-3'<br>(−) 5'Bio-AGTGACAGCAGCATTGTTACAACT-3' | SEQ ID NO: 76<br>SEQ ID NO: 77 |

Listed in Table 2 are a total of 29 sets of oligonucleotide primers based on ESTs of genes of interest. These ESTs are derived from cDNA library #516 which was constructed from breast invasive ductal tumors. #IMAGE is the cDNA clone ID number.

The predicted size of PCR product defined by one set of primers from each EST.

These antisense primers were biotinylated and designated in Table 2 as (−)5' Bio- . . . primer sequence. The sense primers are disignated as (+) 5' . . . primer sequence.

3. Hybridization of Antisense (Biotin-labeled) primers with RNA

Hybridization of biotinylated antisense EST-specific primer with total RNA is carried out using methods known in the art.

Specifically, in this instance the hybridization is carried out in 0.5×sodium chloride/sodium citrate (20×SSC is 3 M sodium chloride and 0.3 M sodium citrate, pH 7.0). Total RNA (50 to 500 μg) suspended in 500 μl of diethylpyrocarbonate (DEPC)-treated water in a 1.5 ml microfuge tube. RNA was incubated at about 65° C. for about 10 minutes in a heating block. Biotinylated antisense primers (25–50 pmoles in 1–2 μl) were added and gently mixed. 20×SSC solution was added to bring the final concentration to approximately 0.5×SSC and mixed. The RNA/primer mixture was incubated at room temperature for about 10 min.

4. Capture of EST-Specific mRNA on Solid Phase

EST-specific mRNA identified by its hybridization to antisense biotinyl-labeled primers is then conjugated to a solid phase using methods known in the art.

Specifically, in this instance, streptavidin coated magnetic beads (100 μl) were washed 3 times with 0.3 ml of 0.5×SSC in a 1.5 ml microfuge tube. The washed magnetic beads were resuspended in 100 μl of 0.5×SSC. The contents of the RNA primer hybridizing reaction were added to the washed magnetic beads and mixed. The mixture was incubated at room temperature for 20–30 minutes with gentle agitation every 5 minutes to resuspend the magnetic beads in solution. The magnetic beads associated with biotinylated primer-RNA were then captured on a magnetic separator for about 2 minutes. The supernatant which contains total RNA not complementary to the primer was transferred to a new 1.5 ml RNase-free tube and stored for later use. The captured magnetic beads were washed 3 times with 0.3 ml of 0.1× SSC per wash. Streptavidin-biotin complex can be substituted with antibody/antigen conjugates, (such as, for example, digoxygenin/anti-digoxygenin magnetic beads.

5. Purification of EST-Specific from Magnetic Beads

Once the EST-specific mRNA is conjugated to the solid phase containing streptadine via biotin, mRNA is separated and isolated as a purified EST-specific mRNA.

Specifically, in this instance, the magnetic beads containing conjugated mRNA were resuspended in 100 μl of RNase-free water by flicking the microfuge tube. After incubating for about 1 minute at about 65° C., the magnetic beads were captured on the magnetic stand for about 2 minutes. The eluted mRNA in solution was transferred to an RNase-free microfuge tube. An additional 100 μl of RNase-free water was added to the magnetic beads for second elusion. The mRNA in combined eluate 200 μl total volume was precipitated by adding 0.1 volume of 3 M sodium acetate, pH 5.2 and 1 volume of isopropanol and incubating at about −20° C. for about 30 minutes. The mRNA was pelleted by centrifugation at 12000×g for 30 min. The mRNA pellet was washed once in 1 ml of 75% ethanol and air-dried for 15 minutes. The mRNA was dissolved in 10 μl of RNase-free, DEPC-treated water, and stored at about −70° C. before use.

After one EST-specific mRNA has been isolated, the supernatant which contains total RNA not complementary to the primer can be reused for sequential isolation of another EST-specific mRNA by hybridizing with a new biotin-labeled antisense primer.

B. Verification of the Integrity of EST-specific mRNAs

In order to assure the integrity of obtained mRNA, the obtained mRNA is subjected to verification using methods known in the art.

Specifically, in this instance the integrity of EST-specific mRNA was verified by RT-PCR and according to Example 5. Results from RT-PCR analysis must confirm the presence and distribution of a particular mRNA in different cells or tissues such as brain, intestine, skin, pancreas, etc.

1. RT-PCR Analysis

Reverse-transcription polymerase chain reaction is known in the art and is generally described in, for example, Nature, 226:1209 (1990).

EST-specific mRNA and total RNA used as control is reverse transcribed using oligo(dT)$_{12-18}$ primers and Superscript II reverse transcriptase reagents obtained from Life Technologies, Gaithersburg, Md.

Specifically, in this instance about 1 μg of total RNA or aliquot of EST-specific mRNA was mixed with about 0.5 μg of oligo(dT)$_{12-18}$ primer in 20 μl of volume containing 20 mM Tris-HCl, pH 8.4, 50 mM KCl, 2.5 μM MgCl$_2$, 10 mM dithiothreitol (DTT), 0.5 mM each of DNTP, and 200 units of Superscript II RNase H⁻ reverse transcriptase. The reaction was incubated for 1 hour at 42° C., followed by heat inactivation at 95° C. for 5 minutes. Thereafter, one-tenth of the first strand cDNA was amplified for 30–35 cycles by PCR using 20 pmoles each of upstream and downstream primers. PCR products were analyzed on 1.5% agarose gels stained with ethidium bromide.

2. Northern Blot Analysis

Northern blot analysis is used to verify the size of the EST-specific mRNA.

Specifically, in this instance EST-specific mRNA, total and poly(A) ⁺RNA (as controls) were separated on 1% formaldehyde denaturing agarose gel and transferred to GeneScreen Plus membrane (NEN Research Products). EST-specific probes were labeled with $\alpha$-$^{32}$P-dCTP to probe the filters. Hybridization was performed at 42° C. in 50% formamide, 5×SSPE, 0.5% SDS, 5×Denhardts' solution, 0.2 mg/ml denatures salmon sperm DNA and radiolabelled probes. Stringency washes were performed in 0.1×SSC, 0.1% SDS at about 62° C. Quality, quantity and size are verified, for example, by molecular weight markers or smearing of RNA on an autoradiograph.

C. Molecular Cloning of EST-specific Full Length cDNAs

After the integrity of EST-specific mRNAs is determined, the molecular cloning of EST-specific full-length cDNAs is undertaken using generally methods and reagents known in the art.

Specifically, in this instance to clone EST-specific cDNA the lambda ZAP-based vectors obtained from Stratagene, La Jolla, Calif., are used according to the current modified protocol.

For first strand cDNA synthesis, the EST-specific mRNA is reverse transcribed using oligo(dT)-Xho I linker-primer [5'-GAGAGAGAGAGAGAGAGAGAGACTCGAG(dT)$_{18}$-3'] (SEQ ID NO: 78) in 10 µl volume in a 0.5 ml RNase-free microcentrifuge tube. 5 µl of the purified EST-specific mRNA is mixed with 50 mM Tris-HCl, pH 7.6, 70 mM KCl, 10 mM MgCl$_2$, 0.6 mM each of dATP, dGTP and dTTP, 0.3 mM 5-methyl dCTP, 0.6 µg of oligo(dT) linker-primer, 8 units of ribonuclease inhibitor. The mRNA template and linker-primer were allowed to anneal for about 10 minutes at about room temperature. One µCi of $\alpha$-$^{32}$P-DATP (800 Ci/mmol, ICN Pharmaceuticals, Costa Mesa, Calif.) and 50 units of reverse transcriptase (RNase H-free) was added to bring the final volume to 10 µl. The reaction was incubated at 42° C. for 1 hour and then stopped by placing on ice.

Second strand cDNA was synthesized by sequentially adding the following components to the first strand reaction (10 µl) on ice: 4 µl of 10×second strand buffer [700 mM Tris-HCl, pH 7.4, 100 mM (NH$_4$)$_2$SO$_4$, 50 mM MgCl$_2$], 1.2 µl second strand dNTP mixture (10 mM dATP, dGTP, dTTP, and 26 mM dCTP), 0.8 units of *E. coli* RNase H, 20 units of *E. coil* DNA polymerase I, and sterile distilled water to bring the final volume to 40 µl. The reaction was incubated for about 2.5 hours at about 16° C.

Besides the protocol described by Stratagene, a cDNA synthesis system from Life Technologies, Inc., is also useful for synthesis of the first strand and second strand cDNA.

Double stranded cDNA was blunt-ended by adding about 4.6 µl of 2.5 mM mixture of dNTPs and 1 unit of cloned pfu DNA polymerase. After incubating at 70° C. for 30 min, the reaction was extracted by phenolchloroform and chloroform, precipitated by adding 1/10 volume of 3 M sodium acetic, pH 5.2, and 2 volumes of ethanol at −20° C., and centrifuging at 15,000 RPM at 4° C. for 20 minutes. After wash with about 70% (v/v) ethanol, the cDNA pellet was dried to completion. Adapter ligation was carried out in 10 µl volume containing 1 µg of EcoRI adapters, 50 mM Tris-HCl, pH 7.4, 10 mM MgCl$_2$, 1 mM DTT, 1 mM and 1 unit of T4 DNA ligase. The ECOLI adapter sequences were 5'-AATTCGGCACGAG-3' (SEQ ID NO: 79) and 5'-phosphorylated CTCGTGCCG-3' (SEQ ID NO: 80). The ligation mixture was incubated overnight or as necessary at about 8° C. and then heat-inactivated at about 70° C. for 30 min, cooled to room temperature and briefly centrifuged.

The adapter-ligated cDNA was phosphorylated by adding 1.5 µl of 10×ligation buffer containing 500 mM Tris-HCl, pH 7.4, 100 mM MgCl$_2$ and 10 mM DTT, 2.0 µl 10 mM rATP, 5 units of T4 polynucleotide kinase and sterile distilled water to about 25 µl volume. The kinase reaction was incubated at about 37° C. for about 30 min, followed by inactivating at about 70° C. for about 30 min. The phosphorylated cDNA (25 µl) was then mixed with 30 µl of Xho I reaction buffer (200 mM NaCl, 15 mM MaCl$_2$), 20 units of Xho I restriction enzyme and sterile distilled water to bring the mixture to the final volume of about 60 µl. The mixture was incubated for about 2 hours at about 37° C. and then cooled to room temperature. The reaction mixture was added 15 µl of 10×STE buffer containing 1 M NaCl, 100 mM Tris-HCl, pH 8.0 and 10 mM EDTA and 75 µl of water to bring the volume to 150 µl. Size fractionation of cDNA was carried out using Sephacryl S-500 drip column following the manufacturer's instructions (Strategene). The size fractionated cDNA was resuspended in 5–10 µl of sterile water.

The cDNA was ligated into the Uni-ZAP XR vector arms which are predigested with EcoR I-Xho I and dephosphorylated according to Stratagene protocol. The cDNA vector ligation was performed in 5 µl volume containing 50 mM Tris-HCl, pH 7.4, 10 mM MgCl$_2$, 1 mM DTT, 1 mM rATP, 0.5 µg of Unit-SAP XR vector, 50 ng cDNA and 1 unit of T4 DNA ligase. Ligation reaction was incubated overnight at about 4° C. Packaging the ligation reaction and plating, and phagemid excision is carried out following manufacturer's protocol (Stratagene).

D. Screening and Sequencing of cDNA Clones

After the EST-specific full-length cDNA is cloned, the cDNA clones are screened for EST-specific sequences and sequenced.

Screening for cDNA clones is conducted using $^{32}$P-radiolabelled probe (oligonucleotide primers or RT-PCR fragments specific to EST) using standard protocol according to Sambrook (Sambrook J., E. F. Fritsch, T. Maniatis, *Molecular Cloning: A Laboratory Manual*, 2ed, Cold Spring Harbor Laboratory Press, Cold Spring Harbor, N.Y. (1989)).

Specifically, in this instance sequencing analysis of selected cDNA clones was carried out with fluorescence cycle sequencing kit (ABI) (Applied Biosystems, Inc.) and analyzed, using Applied Biosystems Model 373A automated DNA sequencer. Both strands of cDNA clones were sequenced and data were analyzed and assembled using Gene Works software obtained from Inteligenetics, Mountain View, Calif. Sequence data were submitted to GenBank after preliminary analysis using BLAST program.

E. Evaluation of the Ouality of cDNA Clones

After the full-length cDNA was sequenced, its quality is evaluated using methods known in the art.

The quality of EST-specific cDNA clones produced by this method is evaluated at several levels. First, the frequency of positive cDNA clones and background signals is compared to obtain the overall efficiency of this method.

Specifically, for full length cDNA evaluation of the method, known mRNA, such as, for example, β-actin gene (1.8 kb) or cystic fibrosis transmembrane conductance regulator (CFTR) gene (6.2 kb) was cloned and analyzed.

The full length is verified by sequencing 5' and 3' ends of cDNA clones and by comparisons with published sequences.

F. Generalized Use of the Method of the Invention

Total cellular RNA isolated from various cell and tissue cultures according to the method of the invention as described above becomes the source for EST-specific mRNA isolation in the different tissue samples.

This method thus is generally useful and becomes practical for full-length cDNA cloning provided that at least a partial cDNA sequence is available. Since the cDNA clones are directly derived from a single mRNA species, screening for a cDNA clone using this method is much easier and cost effective, making it feasible for large scale full-length cDNA cloning. The method also allows for the isolation of mRNA from multigene family using one common primer to isolate possible related mRNAs for the gene family.

Direct PCR screening of the recombinant plasmid is another advantageous feature of this technique since it eliminates membrane hybridization with radiolabelled probes. The technique also shortens time for generating full length clone.

II. Method For Full-Length cDNA Cloning: Multiplex EST Based Approach

The method for full-length cDNA cloning according to the invention have been modified to allow multiplex EST full-length cDNA cloning.

A method of the invention enables a rapid cloning of multiplex EST-specific full-length cDNAs directly from total cellular RNA without library construction. The principle of the method is the same as described in the Section I describing a single EST-based approach. Methods applicable in the single approach are, unless otherwise indicated, equally applicable to the multiplex approach.

In detail, the method for cloning of multiplex full-length cDNA comprises the following steps:

(a) preparing EST-specific antisense primers and biotinylating said primers at the 5' end or at the 3' end;

(b) obtaining total cellular RNA;

(c) submitting total cellular RNA to hybridization with multiple biotinylated EST-specific antisense primer to obtain multiplex EST-specific mRNA;

(d) purifying EST-specific mRNA by contacting a hybridized product with a solid phase, such as, for example, streptavidin coated magnetic beads;

(e) isolating the EST-specific mRNA by eluting and washing the hybridized product from the solid phase;

(f) synthesizing a first cDNA strand by submitting the isolated EST-specific mRNA to reverse transcription using synthesis primers, such as, for example, Not I oligo(dT)18 or oligo d(T)$_{12-18}$;

(g) synthesizing a second cDNA strand by *E. coli* DNA polymerase I in the presence of RNase H;

(h) purifying double-stranded cDNA;

(i) blunting cDNA ends by polymerase, such as $T_4$ DNA polymerase or pfu DNA polymerase;

(j) optionally, ligating a primer adaptor, such as, EcoRI, to the cDNA ends by DNA ligase, such as $T_4$ DNA ligase;

(k) cloning the cDNA into a vector, such as plasmid vector, phage λ vector or mammalian cell expressed plasmid vector;

(l) transforming the vector containing cDNA into bacterial competent cells, for example, by chemical treatment or by electroporation;

(m) screening full-length cDNA clones by PCR amplification or screening full-length cDNA clones by colony hybridization using EST-specific probes, such as, radioactive, chemiluminescent or fluorescent probes; and (n) sequencing DNA of EST-specific full-length cDNA clones.

A diagram of the multiplex EST-specific full-length cDNA cloning is shown in FIG. 12.

A. Enrichment, Purification and Isolation of EST-Specific Full-length mRNA

Methods for enrichment and isolation of EST-specific mRNA are the same as those used for the single approach. FIG. 12 is a schematic diagram of the multiplex isolation of EST-specific mRNAs for library-free system for cloning full-length cDNA. Steps and procedures involved in enrichment and isolation of multiplex EST specific full-length mRNA are described in detail below and in the Examples.

As seen in FIG. 12, EST-specific mRNAs are purified from total cellular RNA by a solid-phase support using biotinylated antisense primers conjugated on solid support, such as streptavidin coated magnetic beads. The purified EST-specific mRNAs are then reverse transcribed into first strand cDNA using oligo(dT) primer. After the second strand synthesis, double stranded cDNA is cloned into a vector. The cDNA clone is then detected by PCR and full-length cDNA are identified by sequence analysis of the recombinant clones.

1. Isolation of Total RNA, Cytoplasmic RNA and poly(A)$^+$ RNA

Total RNA is isolated from cells as described in Section I.

2. EST-Specific oligonucleotide Primers

Examples of oligonucleotide primers used for full-length cDNA cloning are listed in Table 1, as described above in Section I.

3. Capture of Multiplex EST-Specific mRNAs

EST-specific full-length mRNAs were isolated from cytoplasmic RNA by a multiplex isolation. In the initial multiplex isolation, 20 EST-specific biotinylated capture primers were used for the simultaneous isolation and cDNA cloning of multiple mRNAs. Cytoplasmic RNA up to 0.5 mg were resuspended in 500 µl of diethylpyrocarbonate (DEPC)-treated water in a 1.5-ml microcentrifuge tube containing 25 pmoles each biotinylated antisense primers for each EST (total 20×25=500 pmoles of primers). The mixture was incubated for 5 minutes at 65° C. A20×SSC solution was added to a final concentration of 0.5×SSC and mixed by vortex. After incubating at room temperature for 20 minutes with constant rotation, prewashed streptavidin coated magnetic beads (1 mg) in 100 µl of 0.5×SSC was added to the RNA solution. The mixture was incubated at room temperature for 15 minutes with constant rotation to resuspend the magnetic beads in solution. The magnetic beads were captured on a magnetic separator for 1 minute. The supernatant was transferred to a new microcentrifuge tube containing 1 mg of freshly prewashed streptavidin coated magnetic beads for the second capture for 15 minutes at room temperature with constant rotation. The first captured magnetic beads were washed 3 times with 0.3 ml of 0.1×SSC per wash. The magnetic beads were resuspended in 200 µl of DEPC-treated $H_2O$. After incubating at 65° C. for 1 minute, the magnetic beads were captured on the magnetic separator. The mRNA in solution was collected into a 1.5-ml microcentrifuge tube and kept on ice. EST-specific mRNA was eluted from streptavidin magnetic beads from the second capture similarly to the first capture. EST-specific mRNA from the first and second captures was combined and precipitated with 5 µg of glycogen, 0.1 volume of 5 M ammonium acetate, and 2.5 volumes of ethanol at −20° C. The mRNA was pelleted by centrifugation at 14,000 rpm for 15 minutes at 4° C. After washing with 75% ethanol and air-drying, the mRNA was dissolved in 10 μl of DEPC-treated water. The single isolation of EST-specific mRNA was also performed time to time to verify the results from multiplex procedure. For multiplex isolation of EST-specific mRNA, similar procedures as described above for single isolation were followed.

4. Capture of Single EST-specific mRNA
   a) Hybridization of Antisense (Biotin-labeled) primers with RNA Hybridization of biotinylated antisense EST-specific primer with total RNA is carried out using methods known in the art and those described above.

b) Capture of EST-Specific mRNA on Solid Phase

EST-specific mRNA identified by its hybridization to antisense biotinyl-labeled primers is then conjugated to a solid phase using methods known in the art and described above.

c) Purification of EST-Specific mRNA from Magnetic Beads

Once the EST-specific mRNA is conjugated to the solid phase containing streptadine via biotin, mRNA is separated and isolated as a purified EST-specific mRNA as described above.

B. Verification of the Integrity of EST-specific mRNAs

In order to assure the integrity of obtained mRNA, the obtained mRNA is subjected to verification using methods known in the art and those described above.

1. RT-PCR Analysis

Reverse-transcription polymerase chain reaction is known in the art and is generally described in, for example, *Nature*, 226:1209 (1990). Methods used for single approach are equally applicable for multiplex approach.

2. Northern Blot Analysis

Northern blot analysis was used to verify the size of the EST-specific mRNA similarly to the single approach.

C. Molecular Cloning of Multiplex EST-specific Full Length cDNAs

After the integrity of EST-specific mRNAs is determined, the molecular cloning of EST-specific full-length cDNAs is undertaken using generally methods and reagents known in the art.

Specifically, in this instance to clone multiplex EST-specific cDNA, cDNA Synthesis Kit obtained from Life Technologies (Gaithersburg, Md) or cDNA Synthesis Kit obtained from Stratagene (La Jolla, Calif.) were used according to the current modified protocol.

1. First Strand Synthesis

The first-strand cDNA was synthesized from the purified EST-specific mRNAs by reverse transcriptase reaction with an oligo (dT) linker primer containing, for example, PstI restriction site (5'-GGATCCACTGCAGTGGAATTCTTTTTTTTTTTTTTTT-TT-3'), SEQ ID NO: 81 or Not I restriction site (5'-TGTTACCAATCTGAAGTGGGAGCGGCCGCAGAATT-TTTTTTTTTTTTTTTT-3') SEQ ID NO: 82. Briefly, the EST-specific mRNAs in 5 μl DEPC-treated water in a 0.5 ml microcentrifuge tube was incubated at 65° C. for 3 minutes, chilled on ice for 3 minutes, and briefly spun. The first-strand cDNA will be synthesized in 10 μl volume containing the mRNA, 50 mM Tris-HCl, pH 8.3, 75 mM Kcl, 3 mM MgCl$_2$, 500 μM each DNTP, 10 mM DTT, and 10 pmoles of oligo (dT) linker primer, and 50 U of Superscript II RNase H-free reverse transcriptase (Life Technologies for 1 hour at 37° C.

2. Second Strand cDNA Synthesis

The second-strand cDNA was synthesized in an 80 μl volume containing the first strand cDNA, 25 mM Tris-CHl, pH 8.3, 100 mM Kcl, 10 mM (NH4)$_2$SO$_4$, 5 mM MgCl$_2$, 250 μM each of DNTP, 0.15 mM β-NAD, 10 μCi of α-$^{32}$P-dCTP (800 Ci/mmole), 250 U/ml of DNA polymerase I, 8.5 U of RNaseH, and 30 U/ml of DNA ligase (Life Technologies) for 2 hours in a 16° C water bath. After incubation, the reaction was immediately put on ice to stop the reaction.

3. Blunt Ending Double-Stranded cDNA

Double-stranded cDNA was blunt-ended by 1 unit of T$_4$ DNA polymerase (Life Technologies) at 16° C. for 10 minutes. The reaction was extracted by phenol/chloroform and precipitated with ethanol.

4. Restriction Enzyme Digestion of cDNA

The cDNA was digested with 10 units of restriction enzyme PstI or NotI (New England Biolabs) at 37° C. for 4 hours. The reaction was extracted with phenol/chloroform and precipitated with ethanol.

5. Size Fractionation of cDNA

The cDNA size-fractionation was carried out with column chromatography using standard procedure.

The size-selected cDNA was ethanol precipitated prior to ligation into plasmid vector.

6. Preparation of Plasmid Vectors for Full-Length cDNA Cloning

The pUC18 or pBluescript II SK+ plasmid DNA was used for cDNA cloning. The plasmid DNA was digested with SmaI first (blunt end), followed by PstI or NotI (sticky end) (New England Biolabs). The plasmid DNA was purified by phenol/chloroform extraction, gel electrophoresis, and ethanol precipitation. The size-selected cDNA was ligated into the corresponding plasmid DNA digested with appropriate restriction enzymes.

7. Ligation of cDNA With Plasmid Vectors

Ligation reaction was carried out in 10 μl of volume in a 0.5-ml microfuge tube containing the size-selected cDNA, 40 ng of plasmid DNA vector, 1 μl of 10×T4 DNA ligase buffer and 400 units of T4 DNA ligase. The reaction mixture was briefly centrifuged and incubated at 16° C. for 20 hours. The ligation mixture was extracted with phenol/chloroform and precipitated with ethanol. cDNA was dried under vacuum and redissolved in H$_2$O.

8. Bacterial Transformations by Electroporation

Bacterial transformation was carried out using Electro-MAX DH10B cells (Life Technologies) by BioRad Gene Pulser II at 2.5 kV, 200 ohms resistance, and 25 μF capacitance according to the manufacturer's instructions. Aliquots of transformed bacteria were plated on LB agar plates containing 100 μg/ml ampicillin and grown overnight at 37° C. The remaining bacteria was inoculated in 100 ml of LB medium supplemented with 100 μg/ml ampicillin and incubated at 37° C. overnight.

9. Removal of Non-Recombinant Colonies

Optionally, plasmid DNA was isolated from the overnight bacterial culture using a QIAGEN Mini Prep DNA isolation kit according to the manufacturer's instruction. Plasmid DNA was linearized by restriction enzyme and analyzed on agarose gel. Plasmid DNA containing cDNA inserts was isolated, purified by GeneClean kit. The purified plasmid DNA was recirculized by T4 DNA ligase and transformed into bacteria by electroporation using standard procedure.

10. PCR Screening for Full-Length cDNA Clones

For PCR screening, colonies were randomly picked and inoculated in 96-well plates with 50 μl ampicillin-containing LB medium/well. Aliquots of bacterial culture were removed and pooled in rows and columns in 1.5-ml microfuge tubes. The pooling of rows and columns resulted in 20 samples (8 rows and 12 columns) from each 96-well plate bacterial culture. The bacterial samples were screened with PCR by sequentially using different EST-specific primers. One µl each of the pooled bacteria was mixed in 40 µl of water in 0.5-ml PCR tubes, and then boiled for 10 minutes. PCR was carried out in 50 µl with 1 unit of AmpliTaq DNA polymerase (Perkin Elmer). PCR was performed for 30–35 cycles at 94° C. for 30 s, and 72° C. for 1 minute in a GeneAmp PCR System 9700 (Perkin Elmer). PCR products analyzed on 1.5% agarose gels and stained with ethidium bromide.

11. Colony Hybridization for Screening Full-Length cDNA Clones

For colony hybridization, about 4,000 bacteria are spread on 10-cm diameter LB agar plates containing 100 mg/ml ampicillin, and incubated at 37° C. for 16 hours. Replica membranes were prepared with nitrocellulose disk membranes. Hybridization was carried out using EST-specific radiolabelled probes according to the standard protocol.

12. Restriction Digestion of EST-Specific cDNA Clones

EST-specific cDNA clones were digested with restriction enzymes PstI or NotI and electrophoresed on agarose gels to determine the insert sizes. PstI and NotI restriction enzymes were obtained from New England Biolabs, Inc.

13. Sequencing Analysis of EST-Specific Full-Length cDNA Clones

For sequencing reaction, 5–10 cDNA clones for each EST were initially sequenced from both 3' and 5' ends. The DNA sequences generated were aligned and the plasmids with more complete sequences were identified. Further sequencing of the full-length cDNA clones identified were carried out to completion using the primer walking sequencing strategy. ABI Prism Dye Terminator Cycle Sequencing Ready Kits were used for sequencing and the sequencing reactions were analyzed on an ABI 377 automatic sequencing apparatus.

Both strands of cDNA clones were sequenced and data were analyzed and assembled using Gene Works software obtained from Inteligenetics, Mountain View, Calif. Sequence data were submitted to GenBank after preliminary analysis using BLAST program.

E. Evaluation of the Ouality of cDNA Clones

After the full-length cDNA was sequenced, its quality was evaluated using methods known in the art.

The quality of EST-specific cDNA clones produced by this method is evaluated at several levels. First, the frequency of positive cDNA clones and background signals is compared to obtain the overall efficiency of this method.

The full length is verified by sequencing 5' and 3' ends of cDNA clones and by comparisons with published sequences.

F. Generalized Use of the Method of the Invention

Total cellular RNA isolated from various cell and tissue cultures according to the method of the invention as described above becomes the source for EST-specific mRNA isolation in the different tissue samples.

This method thus is generally useful and will become readily accessible for full-length cDNA cloning provided that at least a partial cDNA sequence is available. Since the cDNA clones are directly derived from a single mRNA species, screening for a cDNA clone using this method is much easier and cost effective, making it feasible for large scale full-length cDNA cloning. The method also allows for the isolation of mRNA from multigene family using one common primer to isolate possible related mRNAs for the gene family.

Direct PCR screening of the recombinant plasmid is another advantageous feature of this technique since it eliminates membrane hybridization with radiolabelled probes. The technique also shortens time for generating full length clone.

III. Development of the Method Using Known Sequences of CFTR and β-Actin Genes

The method of the invention was successfully tested and validated on two specific genes encoding CFTR and β-actin.

CFTR gene was selected because it generates a 6.2 kb mRNA and was, therefore, especially suitable for testing the method of the invention in isolating cDNAs for large lmRNAs.

β-actin gene was selected because the sequence is known and it is a high abundance mRNA and thus can be used to readily verify the method.

The principle underlying the novel approach according to the invention was additionally tested, as described above and in examples, using the actin gene family to show that high frequency full-length cDNA clones can be obtained using the library-free system. A biotinylated human β-actin-specific antisense primer was used to isolate β-actin-specific mRNAs from total RNA by streptavidin magnetic bead capture.

First strand cDNA was synthesized by reverse transcriptase reaction using oligo(dT)$_{12-18}$ primer. After second strand synthesis, the double-stranded cDNA was cloned into pUC18 plasmid vector. Recombinant bacterial colonies were picked and placed into 96-well plates. Rows and columns of individual bacterial colonies were pooled and screened by PCR amplification as shown in FIG. 4.

Figure 5:
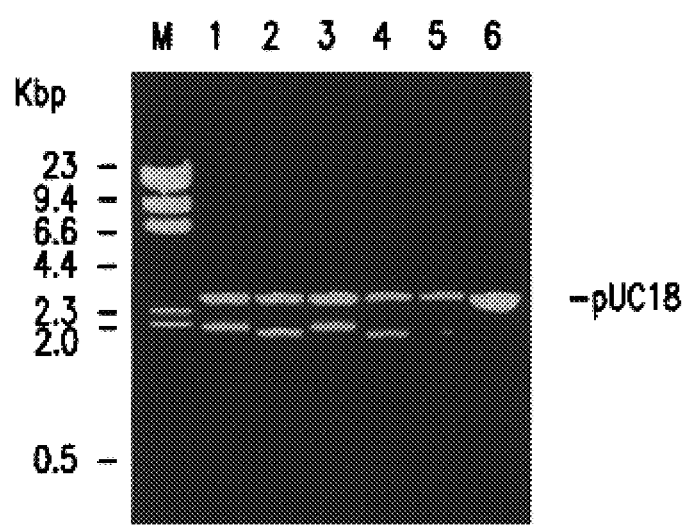
FIG. 5 shows restriction enzyme digestion of recombinant plasmids containing actin cDNA inserts.
Figure 6A:
FIG. 6 shows sequence analysis of plasmid clones containing β-actin (FIG. 6A) and γ-actin (FIG. 6B) cDNA inserts.
Figure 6B:
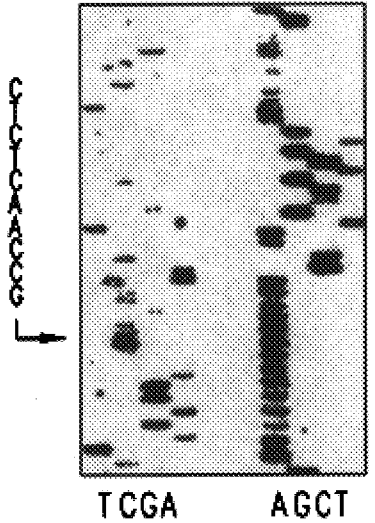

Positive clones were identified by matrix analysis and restriction enzyme digestion illustrated in FIG. 5. Sequence analysis of the 5' and 3' ends of the insert was used as further confirmation of the presence of full-length cDNA as seen in FIG. 6. The PCR screening indicated that ~1% of the primary colonies contained the appropriate inserts.

Figure 4:
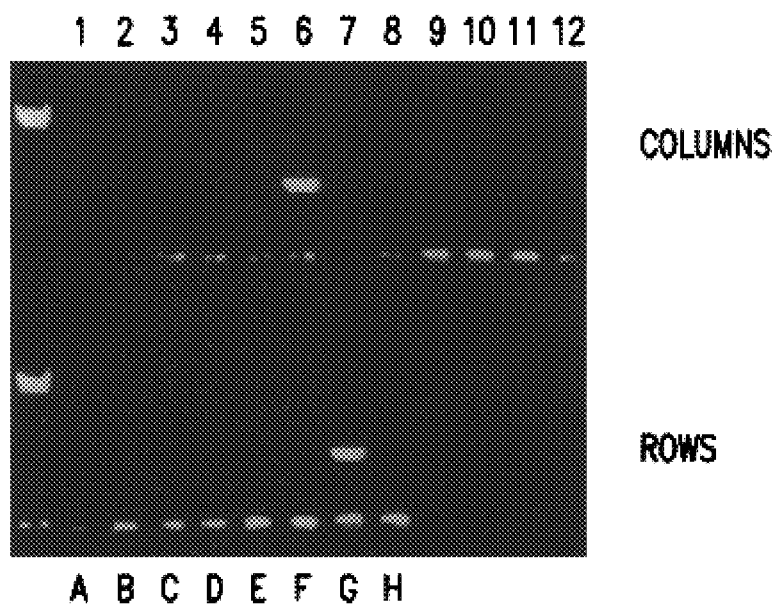
FIG. 4 shows direct screening for human actin cDNA inserts by PCR analysis of pooled bacterial colonies.

Results obtained with screening for human actin cDNA is seen in FIG. 4.

FIG. 4 illustrates direct screening for human actin cDNA inserts by PCR analysis of pooled bacterial colonies. For this study, recombinant colonies were picked and subcultured in 96-well culture dishes. Rows and columns of individual bacterial clones were pooled and the resultant 20 samples per 96-well dish were subjected to PCR analysis. Results of the matrix analysis of one such well dish, seen in FIG. 4, show that column 6 and row G detected β-actin sequences based on PCR with primers derived from β-actin. These results confirm that a plasmid clone in well G6 has a putative β-actin cDNA insert.

Restriction enzyme digestion of recombinant plasmids containing actin cDNA inserts is seen in FIG. 5. In FIG. 5, plasmid DNA was digested with Eco RI and Bam HI restriction enzymes and analyzed on 0.8% agarose gels in 1×TAE buffer. Lanes 1–5 are independent plasmid clones containing the actin cDNA inserts. Lane 6 is linearized pUC18 plasmid DNA without insert (2.6 kb). λ-Hind III fragments were used as the molecular weight marker.

Sequence analysis of plasmid clones containing actin cDNA inserts is illustrated in FIG. 6. For the sequence analysis seen in FIG. 6, plasmid DNA was sequenced with M13 sequencing primers on both 3' and 5' ends. Both β-actin (clone G6) and γ-actin (clone C12) genes are intact at 3' ends. At 5' ends, clone G6 shows +33bp and clone C12 shows —14 bp, as compared with published data.

Sequence analyses of 6 positive clones showed that 4 were the γ-actin cDNA and 2 were β-actin cDNA. Except for the partial clone S7-4, the other 5 clones were all full-length cDNAs when compared to published sequence data seen in Table 3.

Table 3 illustrates sequence analysis of β-actin and γ-actin cDNA clones.

TABLE 3

Sequence Analyses of β-Actin and γ-Actin cDNA Clones

| Gene | Clone | 5' End Sequence | 3' End Sequence |
|---|---|---|---|
| β-Actin* | G6 | +33 bp | 100% Match |
|  | S7-4 | −256 bp | −12 bp |
| γ-Actin** | C12 | −14 bp | 100% Match |
|  | G1 | −21 bp | 100% Match |
|  | N2 | −20 bp | 100% Match |
|  | S7-3 | −20 bp | 100% Match |

*Reference gene: Beta-actin cDNA 1761 bp is available under (GenBank #X00351).
**Reference gene: Gamma-actin cDNA 1918 bp is available under (GenBank #X04098).

Sequence analysis of positive clones seen in Table 3 showed that 83% (5/6 clones) were full-length and that both β-actin and γ-actin full-length cDNAs were isolated by using an mRNA capture primer that shares 90% sequence homology between the two genes.

These results demonstrate that full-length cDNA can be directly cloned at a high frequency from a library-free system. For example, cloning the actin cDNA was accomplished within 5 days thus demonstrating that the technique is rapid and cost effective.

Results from actin cDNA cloning confirm the potential this technique has for isolating full-length cDNA for multigene families or gene homologues across species by using primers with degenerate or conserved sequences for the initial mRNA enrichment.

β-actin and CFTR gene were further investigated in additional studies. Results are described in Examples 7–10.

For these studies, β-actin and cystic fibrosis transmembrane conductance regulator (CFTR) specific mRNAs were purified from total RNA with biotinylated antisense primers and streptavidin magnetic bead capture. Double-stranded cDNA was synthesized and cloned into pUC18 vector. Recombinant colonies were picked and placed in 96-well plates, and directly screened by polymerase chain reaction (PCR) amplification after pooling rows and columns. Positive clones were analyzed by restriction enzyme digestion and sequenced on both ends. Results are similar to those described in FIGS. 4–6.

Analysis of CFTR gene involved screening 288 colonies by PCR. Two clones of these samples (about 0.7%) were identified to contain the CFTR inserts. The results, illustrated in FIGS. 7–10, demonstrate the feasibility of cloning of full-length, gene-specific cDNA from a library-free system and confirm the above-described results.

Figure 7:
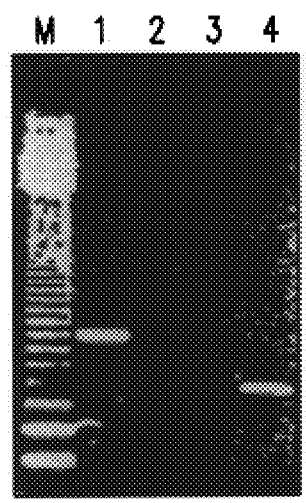
FIG. 7 shows RT-PCR amplification of CFTR (FIG. 8A) and β-actin (FIG. 8B) specific mRNA.

The experimental strategy for the isolation of EST-specific mRNAs and the generations of a cDNA library enriched for those specific sequences is outlined in FIG. 7.

Reverse transcription (RT)-PCR analysis of the mRNA isolated from the total cellular RNA indicated that the mRNA present in the isolates is specific for CFTR and β-actin.

FIG. 7 illustrates RT-PCR amplification of β-actin and CFTR specific mRNAs. For this study, human β-actin or CFTR mRNA was purified individually by hybrid selection with antisense oligonucleotide primers conjugated to solid support. The enriched mRNA was reverse transcribed and then PCR amplified using primers distinct from those used with hybrid selection. FIG. 7, lanes 1 and 2 show β-actin-specific cDNA; lanes 3 and 4 show CFTR-specific cDNA. Amplification in lane 1 was performed with β-actin primers. In lane 2 it was performed with CFTR primers. Lane 3 shows amplification with β-actin primers; lane 4 shows amplification with CFTR primers.

The results seen in FIG. 7 show that mRNA can be specifically purified by hybrid selection with specific antisense primers. The fragment size is shown on the right for β-actin (828 bp) and CFTR (473 bp), respectively. The molecular weight markers are the 123-bp ladders.

After generating the cDNA and cloning it into phage λgt11, phage plaques were analyzed by Southern hybridization with oligonucleotide probes specific for CFTR or β-actin sequences.

Figure 8A:
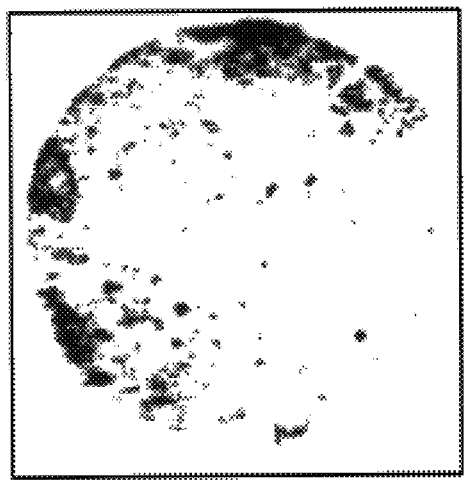
FIG. 8 is autoradiography of the lambda phage screening for cDNA clones containing the CFTR gene (left) or β-actin (right).
Figure 8B:
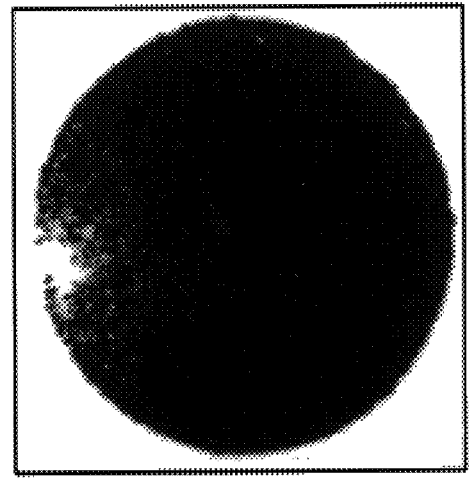

Results are seen in FIG. 8 which shows autoradiography of lambda phage screening for cDNA clones containing the CFTR gene (FIG. 8A) or β-actin (FIG. 8B). Packaged phage was titrated and plated at about 100–150 plaques per 100 mm dish. Phage plaques were transferred to nitrocellulose membrane and hybridized with the 5' end radiolabelled oligonucleotide probes specific for each gene. Exposure to X-ray film was for 24 hours. Positive spots were detected in the range of 22% for β-actin and 12% for CFTR. Gene-specific sequences were confirmed by PCR analysis of phage lygate with CFTR-specific or β-actin-specific primers.

Figure 9:
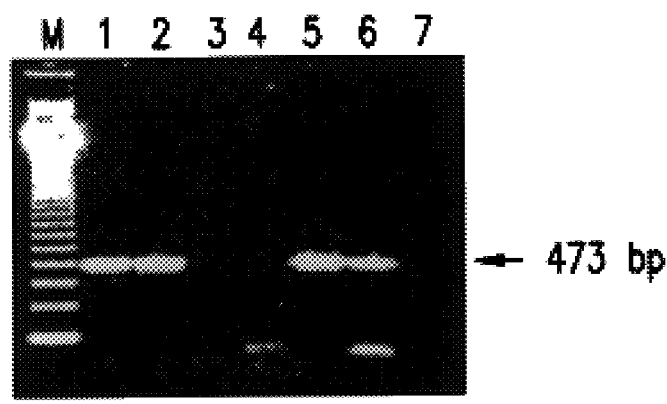
FIG. 9 is PCR analysis of recombinant phage lysate containing CFTR gene.

Since the frequency of gene-specific plaques was ~22% and ~12%, respectively, for β-actin and CFTR, the presence of the gene specific sequences was confirmed by PCR amplification of plaque DNA isolates as seen in FIG. 9.

FIG. 9 is PCR analysis of recombinant phage lysate containing CFTR gene. In this study, phage plaques were picked from top agar exhibiting positive spots by Southern blot analysis. PCR was performed using an aliquot of phage lygate and primers flanking a 473-bp fragment of CFTR gene. Lanes 1–5 show representative samples of recombinant phage lygate; lane 6 was a positive control using cDNA from reverse transcription of total cellular RNA; lane 7 used water as negative control. M lane shows the 123-bp ladders as molecular weight markers. Because the primers for the PCR analysis of the plaque isolates were in the center of the cDNA, the potential is good for retrieving full-length cDNA clones from the plaques. Sequence analysis was used to verify whether the cDNAs are full-length.

FIG. 10 shows screen for human actin specific cDNA clones by colony hybridization. Replica were prepared from an LB agar plate containing approximately 1700 recombinant bacterial colonies, and hybridized with radiolabeled actin probe, and exposed to X-ray film.

FIG. 10 is an example that indicates that cloning efficiency can be increased significantly after non-recombinant colonies were removed by agarose gel electrophoresis. Colonies were transferred to nylon membranes and hybridized with actin-specific radioactive probe.

Results from colony hybridization showed that about 30% of colonies screened were detected by a radiolabelled actin probe.

Figure 11:
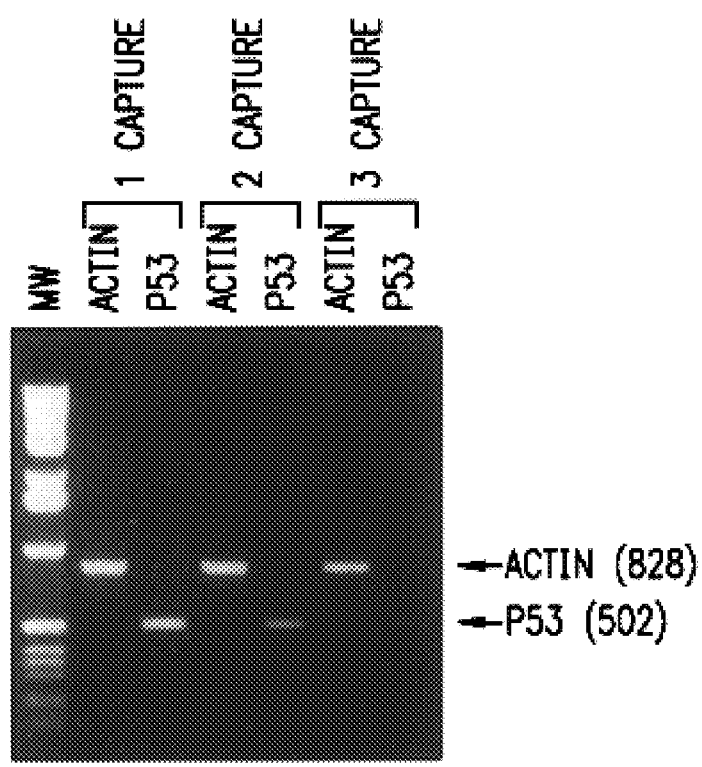
FIG. 11 illustrates increase in the yield of EST-specific mRNA by multiple captures with streptavidin coated magnetic beads.

FIG. 11 is RT-PCR analysis of actin and p53-specific mRNAs from sequentially captured elutes. Biotin-labeled actin (5 pmoles) and p53 (100 pmoles) antisense primers were co-hybridized with 100 μg of total RNA from HeLa cells. The biotin primer-mRNA complex was captured by incubating with streptavidin-coated magnetic beads and eluted from the beads in DEPC-treated water (Capture 1). The RNA supernatant was incubated with the fresh magnetic beads and mRNA was again eluted (Capture 2). This procedure was repeated for a third time (Capture 3). RT-PCR was carried out for 30 cycles. PCR products were analyzed by electrophoresis on 1.5% agarose gels. PCR fragment sizes for actin and p53 cDNAs are indicated on the right. The molecular weight markers are 1 kb ladders.

FIG. 11 demonstrates that double captures increase the yield of EST-specific mRNAs. EST-specific mRNA yields can be increased up to 30% following two sequential incubation of the primer-mRNA hybridization complex with fresh streptavidin coated magnetic beads. Briefly, EST-specific antisense primers were hybridized with cytoplasmic RNA. Primer-mRNA hybridization complex was then captured with magnetic beads and eluted with DEPC-treated water for the first capture. The RNA supernatant was then transferred to a new microcentrifuge tube containing fresh magnetic beads, and the EST-specific mRNA was again captured and eluted as above. The mRNA from the first and second captures were combined and reverse transcribed into first strand cDNA. An example of such a multi-step capture enrichment is indicated in FIG. 11. RT-PCR analysis from the first, second and third mRNA captures suggested that the double capture procedure increase the total amounts of mRNA isolated and deletes the amount of the specific (p53) mRNA in the RNA supernatant.

Actin primers (5' to 3')
ACT(+): ACACCTTCTACAATGAGCTGCG
ACT-Bio(-): CGTCATACTCCTGCTTGCTGAT p53 primers: (5' to 3')
p53(+): TGCATTCTGGGACAGCCAAGTCT
p53 Bio(-): TCTCTCCCAGGACAGGCACAAACA
CFTR primers: (5' to 3')
CF17(+): GAGGGATTTGGGGAATTATTTG
CF22(-): CTTGCTAAAGAAATTCTTTGCTC FIG. 12 is the schematic diagram of the method for multiplex cloning of EXT-specific, full-length cDNAs.

Figure 12B:
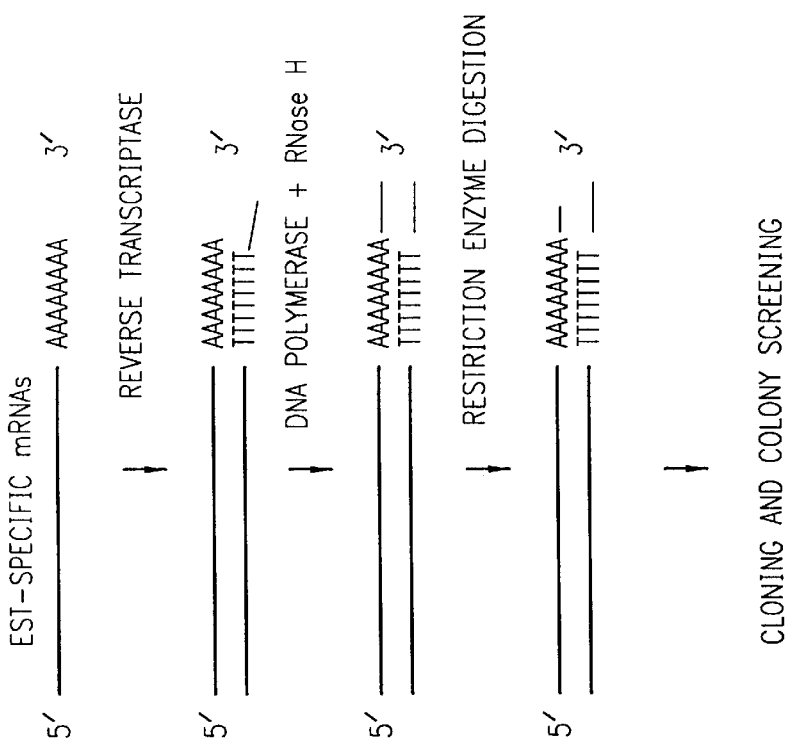
FIG. 12 illustrates a strategy used for multiplex isolation of EST-specific mRNAs.
Figure 12A:
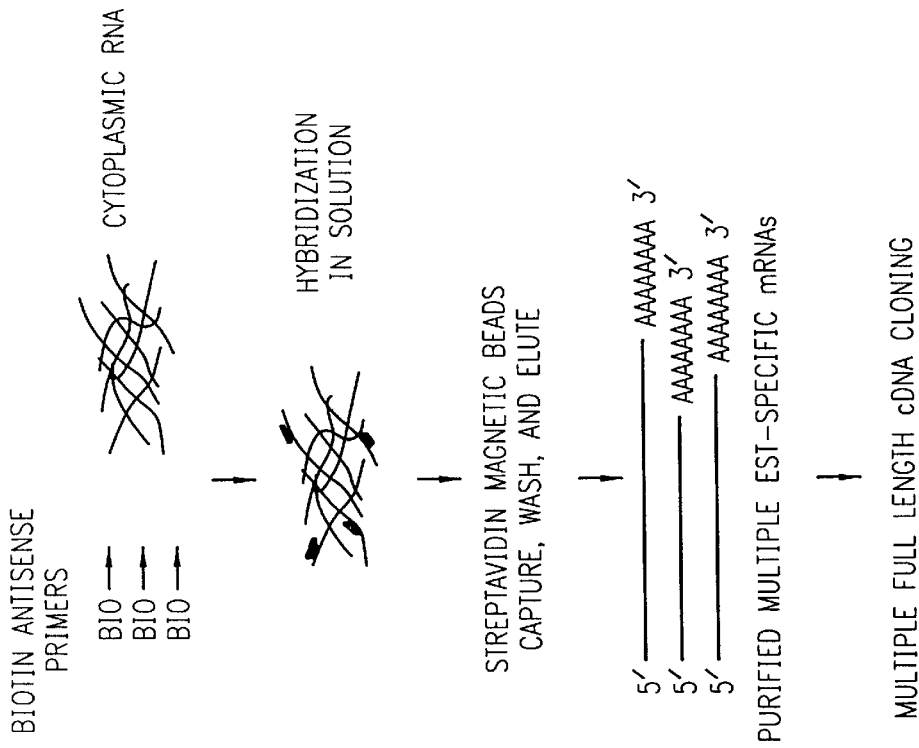

FIG. 12A shows multiple biotinin labeled capture primers up to 20-50 at once were hybridized with RNA. Streptavidin coated magnetic beads was then mixed with the RNA solution. After capture by magnetic separator, the beads were washed with a buffer solution. Purified multiple EST specific mRNA was isolated.

FIG. 12B illustrates full-length cDNA was synthesized by reverse transcriptase, and E. coli DNA polymerase, and cloned into plasmid vectors. PCR and colony hybridization were used for cDNA colony screening.

Figure 13:
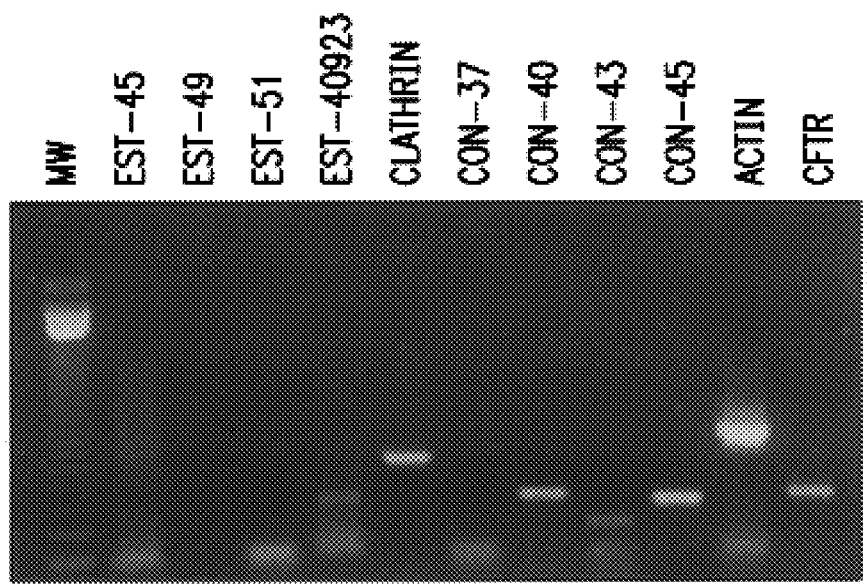
FIG. 13 is the RT-PCR analyses of multiplex EST-specific mRNA isolation.

Multiple EST-specific mRNAs were isolated from 100 μg of total RNA with 11 different biotin-labeled antisense primers in one hybrid-selection capture as seen in FIG. 13. The purified EST-specific mRNAs were reverse transcribed into the first strand cDNA. PCR was carried out using EST-specific primer pairs and analyzed by electrophoresis on 1.5% agarose gels. PCR products from 4 unknown ESTs and 7 known cDNAs are shown here. "Con-" denote connexin family genes. PCR amplifications from the clathrin and CFTR genes represent mRNAs in the 5' end regions of about 6 kbp. The capture prime for Con-37 was based on incorrect sequence information, thus no amplification was expected.

FIG. 13 is the RT-PCR analysis of multiplex EST-specific mRNA isolation.

A multiplex isolation of EST-specific mRNAs was carried out and evaluated with reverse transcriptase (RT) PCR. The capture primers (11 primer shown here) in this initial multiplex isolation are based largely on known sequences that vary in size and expression levels. Different EST-specific mRNAs biotinylated capture primers were simultaneously incubated with cytoplasmic RNA. Est-specific mRNAs were isolated by capture with streptavidin-coated magnetic beads. After reverse transcriptase reaction, aliquots of the first strand cDNA were analyzed by PCR with different EST-specific primers. Results indicate that 8 out of 10 EST-specific mRNAs were present in the multiplex captures. While the conditions for mRNA capture could be optimized, for example, by avoiding high abundance mRNA such as actin in the same capture, the data indicate that mRNAs of different sizes and expression levels could be simultaneously isolated for cDNA cloning. The multiplex cDNAs were then cloned into plasmid vector. Full-length cDNA clones were screened by PCR and colony hybridization.

UTILITY

This invention developed and provides an efficient and cost-effective strategy for generating high quality coding sequences from full-length cDNA clones generated by the method. A library-free system was designed allowing rapid isolation of full-length cDNA clones for, for example, breast cancer-specific ESTs. The technique utilizes hybrid-selection to enrich for EST-specific mRNAs from total RNA with biotin labeled primers and streptavidin magnetic bead capture. Full-length cDNAs are generated from the purified mRNA and cloned into vectors. Results from studies directed at cloning of the actin gene showed that 83% (5/6) of clones contained full-length inserts. The cloning and screening processes took 4-5 days, demonstrating that the technique is rapid and cost-effective.

The technique disclosed in this invention is suitable for large-scale cloning of full-length cDNAs from the breast cancer-specific ESTs and other diseases specific-ESTs. After the relevant full-length cDNAs are cloned, they are sequenced using directed primer walking and random shotgun sequencing strategies.

The method provides an easy, rapid and less laborious procedure for production of large number of full-length cDNAs.

EXAMPLE 1

Isolation of Total Cellular RNA and Poly(A) $^+$RNA

This example describes a method used for RNA isolation from breast tissue cells and from cultured airway epithelial cells.

A. Breast Tissue

Human mammary epithelial cells from normal breast tissue as well as breast cancer cell lines were obtained from American Type Cell Culture (ATCC). Cells were grown on tissue culture dishes in Dulbecco modified Eagle's minimum essential medium (DMEM) supplemented with 10% fetal bovine serum and antibiotics. Total cellular RNA was isolated from cell cultures at near confluence with Trizol Reagents obtained from Gibco BRL, Gaithersburg, Md., according to the manufacturer's instruction. RNA was treated by RNase-free DNase I available from Promega, Madison, Wis., and then extracted with phenol/chloroform to eliminate DNA contamination. Poly(A) $^+$RNA was isolated from total RNA by oligo(dT) cellulose column chromatography using standard methods.

Using this procedure RNA was also isolated from normal breast tissue or breast cancer tissues obtained through the Specialized Program of Research Excellence (SPORE) for Breast Cancer at UCSF.

B. Cultured Airway Epithelial cells

Total cellular RNA was isolated from a human airway epithelial cell line, 16HBE14o-, that expresses wild type CFTR and from HeLa cells RNA was then treated by RNase-free RQ1 DNase (Promega, Madison, Wis.).

Poly(A) $^+$RNA was isolated from total RNA by oligo(dT) cellulose column chromatography using standard methods such as molecular cloning described, for example in Sambrook *Molecular Cloning*, (1989).

Other RNAs from a variety of human tissues, including, infant brain, placenta, and thymus were obtained from ClonTech Laboratories (Palo Alto, Calif.) or directly from biopsy or autopsy samples obtained through the Cell Biology Core of the UCSF Gene Therapy Core Center and treated in the same way as above.

RNA of other tissues not specifically identified above is obtained in the same way.

EXAMPLE 2

Synthesis of Oligonucleotide Primers

This example describes procedure used for synthesis of oligonucleotide primers.

Primers for sequencing reactions used in the primer walking strategy were designed based on newly generated cDNA sequences from full-length cDNA clones. All primers were designed using the OLIGO computer program to check for potential secondary priming sites, and known repeat sequences. Oligonucleotide primers were synthesized with Applied Biosystems, Inc. (ABI) 392 DNA synthesizer through the Biomolecular Resources facility at the University of California, San Francisco. Antisense primers complementary to mRNA were 5' end-labeled with biotin using ABI Aminolink chemistry. Biotinylated primers used for isolating EST-specific mRNAs were purified by polyacrylamide gel electrophoresis (PAGE) following standard procedures.

EXAMPLE 3

This example describes isolation of cytoplasmic RNA.

Cytoplasmic RNA was isolated from cells in culture using NP-40 (Sigma Chemicals) to lyse the cells. Briefly, about $10^7$ cells (e.g., HeLa, 16 HBE) were trypsinized from T75 culture dishes and washed three times with cold (4° C.) Mg- and Ca-free phosphate buffered saline (PBS). Cell pellets were resuspended in 0.5 ml of ice-cold lysis solution of 0.14 M NaCl, 1.5 mM $MgCl_2$, 10 mM Tris (pH 7.8), 10% NP40, and mixed gently by pipetting. After incubating on ice for 5 minutes, nuclei were removed by centrifugation at 2000×g for 5 minutes at 4° C. The supernatant containing the cytoplasmic RNA was transferred to a 1.5-ml microfuge tube. To eliminate residual DNA, the cytoplasmic RNA supernatant was treated by adding 1 μl (1 unit) of RNase-free DNase 1 (Promega) and incubating at 37° C. for 15 minutes. After treatment with RNase-free DNase 1, the RNA supernatant was mixed with 25 μl of 20% SDS (to 1%), 10 μl of 0.5 M EDTA, and 4 μl of 10 mg/ml proteinase K, and incubated in a water bath for 15 minutes at 50° C. The RNA solution was extracted once with 500 μl of phenol/chloroform (1:) and the supernatant was transferred to a fresh 1.5-ml microfuge tube. The RNA was precipitated by addition of 4 μl of 5 M NaCl, 3 μl of 1 M MgCl2 and 2.5 volumes of ethanol. After incubating at −20° C. for 30 minutes, the RNA was pelleted by centrifugation at 10,000×g for 15 minutes at 4° C., washed with 1 ml of cold 70% ethanol, air dried and resuspended diethylpyrocarbonate (DEPC) treated water. RNA was quantitated by UV spectrophotometry.

EXAMPLE 4

Hybridization

This example describes hybridization conditions for hybridization of total RNA with biotinylated antisense primers.

Hybridization of biotinylated antisense EST-specific primer with total RNA was carried out in 0.5×SSC (20×SSC is (or in) 3 M sodium chloride and 0.3 M sodium citrate, pH 7.0). Total RNA (50 to 500 μg) was suspended in 500 μl of DEPC-treated water in a 1.5 ml microfuge tube. RNA was incubated at 65° C. for 10 minutes in a heating block.

Biotinylated antisense primers (25–50 pmoles in 1–2 μl) were added and the mixture was gently mixed. 20×SSC solution was then added to bring the final concentration to approximately 0.5×SSC and mixed. The RNA/primer mixture was incubated at room temperature for about 20–30 minutes. Hybrids were identified and isolated according to Example 5.

EXAMPLE 5

Reverse Transcription (RT)-PCR Analysis

This example describes RT-PCR procedures and conditions used to determine mRNA expression (A) in starting tissues for each EST-specific primer pair and/or using a modified RT-PCR to verify the integrity of obtained mRNAs.

The RT reaction was performed in 50 μl volume containing 5 μg of total RNA, 0.5 μg of oligo(dT)$_{12-18}$ primer (Gibco BRL), 20 mM Tris-HCl, pH 8.4, 50 mM KCl, 2.5 mM $MgCl_2$, 10 mM dithithreitol (DTT), 0.5 mM each dNTP, and 200 U of M-MLV reverse transcriptase (Gibco BRL) for 1 hour at 37 or 42° C. The RT reaction was inactivated by heating to 95° C. for 5 minutes. Following RT, 1 μl of the first-strand cDNA was amplified in 20 μl containing 20 mM Tris-HCl, pH 8.4, 50 mM KCl, 2.5 mM $MgCl_2$, 200 μM dNTPs, 0.001% gelatin, 20 pmoles of each primer and 1 U of AmpliTaq DNA polymerase commercially available from Perkin Elmer.

PCR was performed for 30–35 cycles at 94° C. for 30 s (denaturation), 60° C. for 30 s (annealing), and 72° C. for 1 minute (elongation) in a Perkin-Elmer Cetus DNA Thermal Cycle. PCR products were analyzed on 1.5% agarose gels and stained with ethidium bromide.

EXAMPLE 6

Isolation of EST-Specific Full-Length mRNAs

This example describes a method used for isolation of EST-specific full-length mRNA.

EST-specific full-length mRNA was isolated from total cellular RNA by solid phase capture using biotin/streptavidin magnetic beads.

Total RNA (50 μg) was suspended in 200 μl of diethylpyrocarbonate (DEPC)-treated water in a 1.5 ml microfuge tube containing 25–50 pmoles of biotinylated, antisense primers. The mixture was incubated for 10 minutes at 65° C. A 20×SSC solution was added to a final concentration of 0.5×SSC. After a 20 minutes incubation at room temperature, pre-washed streptavidin coated magnetic beads (0.5–1 mg) in 100 μl of 0.5×SSC were added to the RNA solution. The mixture was incubated at room temperature for 20 minutes with gentle agitation every 5 minutes to resuspend the magnetic beads in solution. The magnetic beads were captured on a magnetic separator for 1 minute. The supernatant was transferred to a new, RNase-free, Eppendorf tube and stored for later use. The captured magnetic beads were washed three times with 0.3 ml of 0.1×SSC per wash. The magnetic beads were then resuspended in 100 μl of RNase-free $H_2O$ by flicking the Eppendorf tube. After incubating at 65° C. for 1 minute, the magnetic beads were captured on the magnetic separator. The mRNA in solution was collected and precipitated with 5 μg of glycogen, 0.1 volume of 5 M ammonium acetate, and 2.5 volumes of ethanol at −20° C. The mRNA was pelleted by centrifugation at 14,000 rpm for 10 minutes at 4° C. After washing in 75% ethanol and air-drying, the mRNA was dissolved in 5 µl of RNase-free DEPC-treated water.

EXAMPLE 7

Synthesis of First and Second Strands cDNA

This example describes methods used for synthesis of the first and second strands of cDNA.

1. First Strand Synthesis

Briefly, the EST-specific mRNAs in 5 µl DEPC-treated water in a 0.5 ml microcentrifuge tube was incubated at 65° C. for 3 minutes, chilled on ice for 3 minutes, and briefly spun. The first-strand cDNA will be synthesized in 10 µl volume containing the mRNA, 50 mM Tris-HCl, pH 8.3, 75 mM KCl, 3 mM $MgCl_2$, 500 µM each dNTP, 10 mM DTT, and 10 pmoles of oligo (dT) linker primer, and 50 U of Superscript II RNase H-free reverse transcriptase (Life Technologies) for 1 hour at 37° C.

2. Second Strand cDNA Synthesis

The Second-strand cDNA was synthesized in an 80 µl volume containing the first strand cDNA, 25 mM Tris-CHl, pH 8.3, 100 mM KCl, 10 mM $(NH4)_2SO_4$, 5 mM $MgCl_2$, 250 µM each of dNTP, 0.15 mM β-NAD, 10 µCi of $\alpha\text{-}^{32}P\text{-}dCTP$ (800 Ci/mmole), 250 U/ml of DNA polymerase I, 8.5 U of RNaseH, and 30 U/ml of DNA ligase (Life Technologies) for 2 hours in a 16° C. water bath.

EXAMPLE 8

EcoRI Linker Ligation

This example describes EcoRI linker ligation procedure.

Ligation into pUC18

The EcoRI linker (5'-pCGACAGCAACGG-3' (SEQ ID NO: 81; 5'-AATTCCGTTGCTGTCG-3') (SEQ ID NO: 82) was obtained from Promega, linker ligation was carried out in 10 µl containing the cDNA, 10 pmoles EcoRI adaptor, 1 mM rATP, 50 mM Tris-HCl, pH 7.5, 7 mM $MgCl_2$, 1 mM DTT, and 4 U of T4 DNA ligase (Strategene, La Jolla, Calif.) for 16 hours at 8° C. T4 DNA ligase was inactivated by incubating for 10 minutes at 65° C. The EcoRI ends were then phosphorylated by adding 1 µl of 10×buffer (500 µM Tris-HCl, pH 7.4; 100 mM $MgCl_2$; 10 mM DTT), 2 µl 10 mM rATP, 5 U of T4 polynucleotide kinase and sterile distilled water to 20 µl for 30 minutes at 37° C. The kinase reaction was stopped by heating to 65° C. for 10 minutes. After linker addition, the double-stranded cDNA was separated by electrophoresis in 1% low-melt agarose, and products larger or equal to 0.5 kb were excised with a scalpel blade. The excised agarose was melted at 65° C. for 15 minutes, digested with the (beta) agarose enzyme for 3 hours at 40° C. (New England Biolabs), phenol/chloroform extracted, and then ethanol precipitated. The cDNA pellet was resuspended in deionized water. The cDNA was ligated with pUC18/EcoRI/BAP in 20 µl according to manufacturer's instruction (Pharmacia).

Ligation into λgt10/λ11

The EcoRI linker ligated cDNA was ligated into the λgt10 vector in case that ligation into the pUC18 plasmid was not successful due to incompatibility of the inserts with host bacteria. The ligation reaction was performed in 5 µl containing: the cDNA, 1 µg of λgt10 EcoRI arms (Promega), 1 mM rATP, 50 mM Tris-HCl, pH 7.5, 7 mM $MgCl_2$, 1 mM DTT, and 2 U of T4 DNA ligase (Stratagene) for 16 hours at 8° C. A 1 µl aliquot of the ligation reaction was incubated with packaging extracts (Promega) according to the manufacturer's specifications. The resulting suspension was titrated on Y1090(r-) bacteria to evaluate the number of recombinants.

EXAMPLE 9

Bacterial Transformation by Electroporation

This example describes conditions used for bacterial transformation by electroporation.

The pUC18 plasmid containing the cDNA inserts was transformed into competent bacteria, obtained from Life Technologies, by electroporation. A 1 µl DNA solution was mixed with 40 µl of competent bacteria on ice for 1 minute. The mixture was transferred to a precooled 0.2 cm BioRad Gene Pulser Cuvette and electroporated at 2.5 kV, 200Ω resistance, and 25 µF capacitance. SOC medium (1 ml) was added immediately after the pulse and the bacteria was transferred to a 15-ml Falcon tube, and incubated for 37° C. for 1 hour with agitation (250 rpm). Bacteria was plated on LB agar plates containing 100 µg/ml ampicillin, X-GAL and IPTG (for blue/white screening), and then grown overnight at 37° C.

EXAMPLE 10

Construction of the Capture Primer Enriched EST-Specific cDNA Libraries

This example describes methods used for construction of the EST-specific cDNA libraries.

EcoRI adaptors (5'-pCGACAGCAACGG-3' (SEQ ID NO: 82, as in Example 8); 5'-AATTCCGTTGCTGTCG-3' (SEQ ID NO: 83, as in Example 8))(Promega) was used for ligation to the double-stranded cDNA. The EcoRI adaptor was only added to the 5' end of the cDNA, because the Not I-oligo(dT)$_{18}$ primer is biotinylated at 5' end. Ligation reaction was carried out in 10 µl containing the cDNA, 10 pmole EcoRI adaptor, 1 mM rATP, 50 mM Tris-HCl, pH 7.5, 7 mM $MgCl_2$, 1 mM DTT, and 4 units of T4 DNA ligase (Stratagene, La Jolla, Calif.) for 16 hours at 8° C. T4 ligase was inactivated by incubating for 10 minutes at 65° C. and by a brief centrifugation. The EcoRI ends were then phosphorylated by adding 1 µl of 10×buffer (500 mM Tris-HCl, pH 7.4; 100 mM $MgCl_2$; 10 mM DTT), 2.0 µl of 10 mM rATP, 5 units of T4 polynucleotide kinase and sterile distilled water to 20 µl volume for 30 minutes at 37° C. After incubation for 10 minutes at 65° C., the reaction mixture was extracted and precipitated. The resultant cDNA fragment was washed with 75% ethanol, vacuum dried, and redissolved in sterile distilled water.

Not I digest was performed in 20 µl containing the cDNA, 6 mM Tris-HCl, pH 7.6; 6 mM $MgCl_2$; 150 mM NaCl; 1 mM DTT; 0.1 mg/ml acetylated BSA (Promega); and 5 U of Not I enzyme (Promega) for 1.5 hours at 37° C. The reaction mixture was inactivated by incubation at 65° C. for 10 min. The cDNA molecules were purified by size fractionation using 1-ml Sephacryl S-500 (Pharmacia) columns and then precipitated with 0.1 volume of 3 M sodium acetate, pH 5.2 and 2 volumes of ethanol at −20° C. After washing with 75% ethanol, the cDNA product was vacuum dried.

The cDNA molecules were ligated into the λgt11 Sfi-Not I vector digested with Eco RI and Not I (Promega). The ligation reaction was performed in 5 µl of volume containing the cDNA, 1 µg of λgt11 EcoRI/Not I arms, 1 mM rATP, 50 mM Tris-HCl, pH 7.5; 7 mM $MgCl_2$; 1 mM DTT; and 2 U of T4 DNA ligase (Stratagene) for 16 hours at 8° C. A 1 μl aliquot of the ligation reaction was incubated with packaging extracts (Promega), according to the manufacturer's specifications. The resulting suspension was titrated on y1090(r-) bacteria to evaluate the number of recombinants. Background was estimated by self-ligation of the vector arms, followed by packaging and titration.

EXAMPLE 11

Characterization of the Capture-Primer Enriched EST-specific cDNA Libraries

This example describes method used for characterization of the cDNA libraries.

The phage clones were transferred to nitrocellulose filters for library screening. EST-specific oligonucleotide probes radiolabelled with [γ-$^{32}$P]ATP at the 5' end with T4 kinase were used. Phage DNA was prepared from isolated plaques and analyzed by restriction enzyme digestion and Southern blot hybridization. The cDNA inserts were subcloned into the pGEM 13zf plasmid (Promega, Madison, Wis.) for sequence analysis. Both strands of cDNA clones were sequenced and data were analyzed and assembled using Gene Works software (Inteligenetics, Mountain View, Calif.). Sequence data were submitted to GenBank after preliminary analysis using the BLAST program.

EXAMPLE 12

Screening for Recombinant Colonies

This example describes screening for colonies for EST-specific cDNA inserts.

Recombinant colonies containing EST-specific cDNA inserts were directly screened by PCR amplification of rows/columns-pooled bacterial colonies plated in a 96-well matrix array. White bacterial colonies were randomly picked and inoculated in 96-well plates with 100 μl selective LB medium/well. The bacteria were incubated at 37° C. for 2–3 hours with gentle agitation (150 rpm). A 10 μl/well aliquot of bacterial culture was removed and pooled in terms of rows and columns on the matrix array using a multiple channel pipetter. The pooled columns or rows were collected into microcentrifuge tubes. Pooling results in 20 samples (8 rows and 12 columns) for each 96-well plate.

For PCR screening analysis, 1 μl of the pooled bacteria were mixed in 15 μl of deionized water in 0.5-ml PCR tubes, and then boiled for 10 minutes. Denatured bacterial DNA samples were immediately chilled on ice for 5 minutes, followed by a brief centrifugation. PCR was carried out in 20 μl containing denatured bacteria-derived DNA, 20 mM Tris-HCl, pH 8.4, 50 mM KCl, 2.0 mM $MgCl_2$, 200 μM dNTPs, 0.001% gelatin, 20 pmoles of each primer, and 0.5 U of AmpliTaq DNA polymerase (Perkin Elmer). PCR was performed for 30–35 cycles at 94° C. for 30 s, 60° C. for 30 s, and 72° C. for 1 minute in a DNA Thermal Cycler (Perkin-Elmer Cetus). PCR products were analyzed on 1.5% agarose gels stained with ethidium bromide. Wells containing recombinant clones were identified based on positive signals detected by PCR. The clones were subcultured and the plasmids isolated from a 5 ml overnight culture using Wizard Plus SV Minipreps DNA Purification System (Promega) specified by the manual instructions.

Plasmid DNA containing the EST-specific cDNA insert was digested with Bam HI and/or Eco RI enzymes and analyzed on 0.8% agarose gels stained with ethidium bromide. Results from restriction analysis indicated the plasmids that contain longest cDNA inserts for the same EST. These plasmids were subjected to sequence analysis as described in Example 12.

EXAMPLE 13

DNA Sequence Analysis

This example describes the method used for analysis of DNA sequence.

Directed primer walking strategy for cDNA sequencing was used. The primer walking approach required the lowest possible redundancy of two readings per base pair. This approach was the most favored for the sequencing of small inserts, such as is the case with most cDNA clones.

First, breast cancer-specific EST-associated partial clones were sequenced while the cloning of full-length cDNAs was under way. The partial clones, with an average size of 600 bp, were obtained from the Integrated Molecular Analysis of Genomes Consortium (IMAGE). Plasmid DNA was purified with a Wizard SV Minipreps DNA Purification System (Promega).

To ensure high quality sequences, at least two independent full-length cDNA clones per corresponding EST were sequenced to completion. Both forward and reverse strands of cDNA inserts were sequenced using the primer walking sequencing scheme described in *Biotechniques*, 15:714 (1993), in which newly generated sequences by one primer were confirmed by second strand sequencing using a reverse primer.

EXAMPLE 14

Verification of Full-Length Coding Sequences

This example describes procedures used for verification of coding sequences of full-length cDNA.

Clones containing the longer inserts, as identified by restriction digest analysis, were sequenced. These longer clones provided more sequence information, thus a higher probability that a more complete coding sequence will be generated. Results from computer analyses indicated whether a cDNA insert contains the complete coding sequence of the expressed gene. The presence of 3'poly(A) tail, poly(A) splicing signal (AATAAA) (SEQ ID NO: 84), start and stop cordons, the ORF, and the predicted gene structure provided evidence for the extent to which the coding sequence is complete.

The 5' RACE (Rapid Amplification for cDNA Ends) method was used to verify that the final sequences generated from the full-length cDNA clones were complete. The 5' cDNA ends of the corresponding ESTs were generated using the 5' RACE System (Version 2.0, Life Technologies, Inc., Gibco BRL) to amplify the cDNA 5' ends according to the manufacturer's instructions. First strand cDNA was synthesized from poly(A) $^{+}$RNA using a gene-specific primer (GSP1) near 5' end region. The first strand cDNA was purified with GlassMax DNA isolation spin cartridge and then tailed with homopolymeric C by 3' terminal deoxynucleotide transferase (3'TdT). The terminal transferase reaction was stopped by heating for 10 minutes at 65° C., followed by a brief centrifugation.

PCR was performed with an abridged anchor primer and a gene-specific primer, GSP2 (internal to the GSP1), according to the manufacturer's instructions (Life Technologies, Gibco BRL). PCR products were analyzed by aragose gel electrophoresis and then inserted into TA-cloning vectors (In Vitorgen, San Diego). The 5' RACE-derived fragments were sequenced and compared to the full-length cDNA sequences.

What is claimed is:

1. A method for cloning and sequencing of EST-specific full-length cDNA clones, said method comprising steps:
   (a) preparing EST-specific antisense primers and biotinylating said primers at the 5' end or at the 3' end;
   (b) obtaining total cellular RNA;
   (c) submitting total cellular RNA to hybridization with single biotinylated EST-specific antisense primer to obtain single EST-specific mRNA;
   (d) purifying EST-specific mRNA by contacting a hybridized product with streptavidin coated magnetic beads;
   (e) isolating the EST-specific mRNA by eluting and washing the hybridized product from the solid phase;
   (f) synthesizing a first cDNA strand by submitting the isolated EST-specific mRNA to reverse transcription using Not I oligo(dT)$_{18}$, Pst I oligo(dT)$_{18}$, or oligo d(T)$_{12-18}$ as synthesis primer;
   (g) synthesizing a second cDNA strand by E. coli DNA polymerase I in the presence of RNase H; or by a poly(dT) using 3' terminal deoxynucloeotide transferase and synthesizing a second cDNA strand by using T7 DNA polymerase;

(h) purifying double-stranded cDNA by ethanol precipitation or column size fractionation;

(i) blunting cDNA ends by $T_4$ DNA polymerase or by pfu DNA polymerase;

(j) ligating EcoR1 adaptor primers to the cDNA ends by $T_4$ DNA ligase;

(k) cloning the cDNA into plasmid vector or phage λ vector;

(l) transforming the vector containing cDNA into bacterial competent cells by chemical treatment or by electroporation;

(m) screening full-length cDNA clones by PCR amplification or by colony hybridization using radioactive chemiluminescent or fluorescent probes; and (n) sequencing DNA of EST-specific full-length cDNA clones.

2. A method for cloning and sequencing of multiplex EST-specific full-length cDNA clones comprising steps:

(a) preparing EST-specific antisense primers and biotinylating said primers at the 5' end or at the 3' end;

(b) obtaining total cellular RNA;

(c) submitting total cellular RNA to hybridization with multiple biotinylated EST-specific antisense capture primers for multiplex isolation of EST-specific mRNAs;

(d) purifying EST-specific mRNA by contacting hybridized product with streptavidin coated magnetic beads;

(e) isolating the EST-specific mRNA by eluting and washing the hybridized product from the solid phase;

(f) synthesizing a first cDNA strand by submitting the isolated EST-specific mRNA to reverse transcription using Not I oligo(dT), PstI oligo $(dT)_{18}$ or oligo $(dT)_{12-18}$ as synthesis primer;

(g) synthesizing a second cDNA strand by $E.\ coli$ DNA polymerase I in the presence of RNase H;

(h) purifying double-stranded cDNA by ethanol precipitation and by column size fractionation;

(i) blunting cDNA ends by $T_4$DNA polymerase or by pfu DNA polymerase;

(j) cloning the cDNA into plasmid vectors;

(k) transformation into bacterial competent cells by chemical treatment or by electroporating;

(l) screening full-length cDNA clones by PCR amplification;

(m) or screening full-length cDNA clones by colony hybridization using radioactive probes;

(n) DNA sequencing of EST-specific full-length cDNA clones.

3. The method of claim 2, wherein there are about 20 to about 100 EST-specific antisense capture primers.

4. A method for sequencing and cloning of EST-specific full-length cDNA clones, said method comprising steps:

(a) preparing EST-specific antisense primers and biotinylating said primers at the 5' end or at the 3' end;

(b) obtaining total cellular RNA;

(c) submitting total cellular RNA to hybridization with single biotinylated EST-specific antisense primer to obtain single EST-specific mRNA;

(d) purifying EST-specific mRNA by contacting a hybridized product with streptavidin coated magnetic beads;

(e) isolating the EST-specific mRNA by eluting and washing the hybridized product from the solid phase;

(f) synthesizing a first cDNA strand by submitting the isolated EST-specific mRNA to reverse transcription primed by oligo(dT)-based primer;

(g) synthesizing a second cDNA strand using a polymerase;

(h) purifying double-stranded cDNA; and (i) cloning the cDNA.

5. The method of claim 4 wherein the synthesis of step (f) comprises synthesis of a first strand cDNA by reverse transcription using Not I oligo$(dT)_{18}$, Pst I oligo$(dT)_{18}$, or oligo $d(T)_{12-18}$ as synthesis primer and synthesis of the second strand cDNA using $E.\ coli$ DNA polymerase I in the presence of RNase H or by poly(dT) using 3' terminal deoxynucloeotide transferase and T7 DNA polymerase I.

6. The method of claim 5 wherein the primers are designed based on ESTs and labeled at 5' or 3' end.

7. The method of claim 6 wherein the EST-specific primers are designed based on the human chromosome 7 EST database and breast cancer-specific ESTs and labeled at their 5' end or 3' end with biotin.

8. The method of claim 7 wherein the primers are biotinylated.

9. The method of claim 8 wherein the second cDNA strand is synthesized by using $E.\ coli$ DNA polymerase I.

10. The method of claim 9 wherein the second cDNA strand is synthesized by using T7 DNA polymerase I.

11. The method of claim 8 wherein the double stranded cDNA is purified.

12. The method of claim 11 wherein cDNA ends are blunted by a polymerase.

13. The method of claim 12, wherein the blunting polymerase is $T_4$ DNA or pfu DNA polymerase.

14. The method of claim 13, wherein the cDNA is cloned into a vector.

15. The method of claim 14 wherein the vector is a plasmid vector, phage λ vector or a mammalian cell expressed plasmid vector.

16. The method of claim 15 wherein the vector containing cDNA is transformed into bacterial competent cells.

17. The method of claim 16 wherein the vector is transformed by chemical treatment or electroporation.

18. The method of claim 17 wherein the full-length cDNA clones are screened by polymerase chain reaction amplification or by colony hybridization.

19. The method of claim 18 wherein the hybridization utilizes a EST-specific radioactive, chemiluminescent or fluorescent probe.

20. The method of claim 19 wherein the full-length cDNA clones are sequenced.

* * * * *

```
                             SEQUENCE LISTING

<160> NUMBER OF SEQ ID NOS: 96

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 1
tctaggcaga gtctcaggag ca                                                  22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 2
agggaggttt gtcctgaaat gg                                                  22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 3
acttggctcc tctcacttgg aa                                                  22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 4
gtgtagtagt aaagaggaga gg                                                  22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 5
ttcaacctca gcctcccctt ca                                                  22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 6
ccatgggttc atgtgtgatt ga                                                  22
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 7
cttagcaagg gcaggctgat gt                                            22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 8
ctccaaccat ggcactcaga ta                                            22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 9
aggacaggta ggaggatggg gt                                            22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 10
ctctcctctc actcattctc tt                                            22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 11
tctgggtcag tgatagagaa tg                                            22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 12
aggatggcat cctatgaaat gc                                            22

<210> SEQ ID NO 13
<211> LENGTH: 22
<212> TYPE: DNA
<213> ORGANISM: Artificial Sequence
<220> FEATURE:

<223> OTHER INFORMATION: Description of Artificial Sequence: primer

<400> SEQUENCE: 13
ggatgatgac ttggtgtgaa tc                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 14
ctgtgaagac cgtgagatga tt                                              22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 15
ttgagacact aacctcccg g                                                21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 16
ctagggaagt ttccattgtt cc                                              22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 17
gtcaaggatg actctccaat tt                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 18
ttccctcaag cttccagttt ac                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 19
gaaggagagc aagttcaaga gc                                              22

```
<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 20
ccatgacaga cctgaagaca tg                                              22

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 21
gtggcttgta aatcattctc ctgt                                            24

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 22
tctgagggtt tattggtcag gg                                              22

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 23
ttccattgct gcagatgtaa agg                                             23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 24
tgtgtcttcc attctgcttt gc                                              22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 25
tgtcttctaa ggatggtctt cca                                             23

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: primer
```

<400> SEQUENCE: 26
gattaagttc atgcatttct acac                                    24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 27
gctttatagt gtaacagaat gggc                                    24

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 28
cgtttctaaa gaacagagag gcg                                     23

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 29
tgaaggggta ctgtacttta ttcc                                    24

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 30
actagactga gagccagtgt ga                                      22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 31
aggggagccg aattctacat ttc                                     23

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 32
tttattacag cagcaactga ggcg                                    24

<210> SEQ ID NO 33
<211> LENGTH: 23

```
<212> TYPE: DNA
<213> ORGANISM: Artificial Sequence
<220> FEATURE:
<223> OTHER INFORMATION: Description of Artificial Sequence: primer

<400> SEQUENCE: 33
gactggatgt gcctttatcc tct                                            23

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 34
atacgccttc tcatccacca ga                                             22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 35
gagctgcaag tgatgacagc at                                             22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 36
gcggtgatga ctcttgaact tc                                             22

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 37
gtgaatgtga agttccccat ctt                                            23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 38
acagaggtgt caagggtagg a                                              21

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 39
```

```
ggccgatttt gtccagaatt atct                                          24

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 40
tcttgcgagg aggtcgtgag aa                                            22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 41
aagtaacagc agccgtcttg ga                                            22

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 42
gagaacacaa ggactctac                                                19

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 43
tgtccacact gactggaata ct                                            22

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 44
cggaatgatc tcagtaacta ttttcc                                        26

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 45
gcacaaggat gtcacgggat att                                           23

<210> SEQ ID NO 46
<211> LENGTH: 22
<212> TYPE: DNA
<213> ORGANISM: Artificial Sequence
```

```
<220> FEATURE:
<223> OTHER INFORMATION: Description of Artificial Sequence: primer

<400> SEQUENCE: 46
ccacacctac acacctctac ac                                              22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 47
tccaagacct ggcctccctt aa                                              22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 48
ctggcaactg cagggcactg t                                               21

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 49
caaatacagt taataagaga gtattag                                         27

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 50
tgcttgatgg tgcctccgat ct                                              22

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 51
gggcaatcat gtcatttaat aatca                                           25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 52
ctcaaaagtc catgacaaat agaag                                           25
```

```
<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 53
cgcagaatca aagtctgtac ttcaa                                              25

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 54
cccaaaccct tatgcatttt atgc                                               24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 55
catgaagcta cagatcttag tgct                                               24

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 56
ccagggcctt ggactgtttc                                                    20

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 57
tcattatctc taccgtggtt ctgt                                               24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 58
tctacctgca ttacaaaccc ctat                                               24

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: primer
```

```
<400> SEQUENCE: 59
agtgtcaggg tgaccaggaa tt                                          22

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 60
gcctggagtt aagtattctg aaat                                        24

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 61
agcgggccgt atctccttgt c                                           21

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 62
gacaaaatag ggatagggag attc                                        24

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 63
gggagagaaa ccctatgagt gt                                          22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 64
agaatcttgg cagatctgaa gg                                          22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 65
tgatcatctt tggggtggca ga                                          22

<210> SEQ ID NO 66
```

```
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 66
cttgttctga aactggcagc tc                                           22

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 67
tcacagcatg gtggcctcta g                                            21

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 68
gacacaaatt caaatggctg tggt                                         24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 69
cttagtgtta ggttgtctga tgag                                         24

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 70
gggaatgcta caatgtcaga ca                                           22

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 71
gaacgaccta gaagagtgct tg                                           22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 72
```
aggagcagcc attgattttg tg                                          22

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 73
agatgatttc ccttctgtaa ctcc                                        24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 74
cttaagtggg gtttcagaac agat                                        24

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 75
tctcagctct gcagctgtct g                                           21

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 76
ccaacatacc cctttctggt gt                                          22

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 77
taaacggaat cacgtatggt tctt                                        24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 78
agtgacagca gcattgttac aact                                        24

<210> SEQ ID NO 79
<211> LENGTH: 44
<212> TYPE: DNA

```
<213> ORGANISM: Artificial Sequence
<220> FEATURE:
<223> OTHER INFORMATION: Description of Artificial Sequence: primer

<400> SEQUENCE: 79
gagagagaga gagagagaga ctcgagtttt tttttttttt tttt                44

<210> SEQ ID NO 80
<211> LENGTH: 13
<212> TYPE: DNA
<213> ORGANISM: Artificial Sequence
<220> FEATURE:
<223> OTHER INFORMATION: Description of Artificial Sequence: ECOLI
      adapter

<400> SEQUENCE: 80
aattcggcac gag                                                  13

<210> SEQ ID NO 81
<211> LENGTH: 9
<212> TYPE: DNA
<213> ORGANISM: Artificial Sequence
<220> FEATURE:
<223> OTHER INFORMATION: Description of Artificial Sequence: ECOLI
      adapter

<400> SEQUENCE: 81 ctcgtgccg                                                        9

<210> SEQ ID NO 82
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 82
ggatccactg cagtggaatt ctttttttttt tttttttttt                    39

<210> SEQ ID NO 83
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 83
tgttaccaat ctgaagtggg agcggccgca gaattttttt tttttttttt t        51

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: EcoRI
      linker

<400> SEQUENCE: 84
cgacagcaac gg                                                   12

<210> SEQ ID NO 85
<211> LENGTH: 16
<212> TYPE: DNA
<213> ORGANISM: Artificial Sequence
<220> FEATURE:
<223> OTHER INFORMATION: Description of Artificial Sequence: EcoRI
      linker
```

<400> SEQUENCE: 85
aattccgttg ctgtcg                                                    16

<210> SEQ ID NO 86
<211> LENGTH: 6
<212> TYPE: DNA
<213> ORGANISM: Artificial Sequence
<220> FEATURE:
<223> OTHER INFORMATION: Description of Artificial Sequence: poly A
      splicing signal

<400> SEQUENCE: 86 aataaa                                                                6

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: actin
      primer

<400> SEQUENCE: 87
acaccttcta caatgagctg cg                                             22

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: actin
      primer

<400> SEQUENCE: 88
cgtcatactc ctgcttgctg at                                             22

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: p53 primer

<400> SEQUENCE: 89
tgcattctgg gacagccaag tct                                            23

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: p53 primer

<400> SEQUENCE: 90
tctctcccag gacaggcaca aaca                                           24

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: CFTR primer

<400> SEQUENCE: 91
gagggatttg gggaattatt tg                                             22

```
<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: CFTR primer

<400> SEQUENCE: 92
cttgctaaag aaattctttg ctc                                              23

<210> SEQ ID NO 93
<211> LENGTH: 10
<212> TYPE: DNA
<213> ORGANISM: Artificial Sequence
<220> FEATURE:
<223> OTHER INFORMATION: Description of Artificial Sequence: actin cDNA
      insert

<400> SEQUENCE: 93
cgcctgcgcc                                                             10

<210> SEQ ID NO 94
<211> LENGTH: 10
<212> TYPE: DNA
<213> ORGANISM: Artificial Sequence
<220> FEATURE:
<223> OTHER INFORMATION: Description of Artificial Sequence: actin cDNA
      insert

<400> SEQUENCE: 94
ttccacacgt                                                             10

<210> SEQ ID NO 95
<211> LENGTH: 10
<212> TYPE: DNA
<213> ORGANISM: Artificial Sequence
<220> FEATURE:
<223> OTHER INFORMATION: Description of Artificial Sequence: actin cDNA
      insert

<400> SEQUENCE: 95
ctctcaaccg                                                             10

<210> SEQ ID NO 96
<211> LENGTH: 10
<212> TYPE: DNA
<213> ORGANISM: Artificial Sequence
<220> FEATURE:
<223> OTHER INFORMATION: Description of Artificial Sequence: actin cDNA
      insert

<400> SEQUENCE: 96
ccaatgccgt                                                             10
```